US008504908B2

(12) United States Patent
Chisholm

(10) Patent No.: US 8,504,908 B2
(45) Date of Patent: Aug. 6, 2013

(54) COMPUTER-IMPLEMENTED METHODS DISPLAYING, IN A FIRST PART, A DOCUMENT AND IN A SECOND PART, A SELECTED INDEX OF ENTITIES IDENTIFIED IN THE DOCUMENT

(75) Inventor: Alastair Chisholm, Scotland (GB)

(73) Assignee: ITI Scotland, Limited, Glasgow (GB)

( * ) Notice: Subject to any disclaimer, the term of this patent is extended or adjusted under 35 U.S.C. 154(b) by 196 days.

(21) Appl. No.: 12/738,751

(22) PCT Filed: Oct. 17, 2008
(Under 37 CFR 1.47)

(86) PCT No.: PCT/GB2008/050959
§ 371 (c)(1),
(2), (4) Date: Jan. 18, 2011

(87) PCT Pub. No.: WO2009/050521
PCT Pub. Date: Apr. 23, 2009

(65) Prior Publication Data
US 2012/0011428 A1 Jan. 12, 2012

(30) Foreign Application Priority Data

Oct. 17, 2007 (GB) .................................. 0720304.5
Feb. 20, 2008 (GB) .................................. 0803073.6

(51) Int. Cl.
*G06F 17/00* (2006.01)

(52) U.S. Cl.
USPC ........................................................ 715/230

(58) Field of Classification Search
USPC ................................. 715/229, 230, 231, 232
See application file for complete search history.

(56) References Cited

U.S. PATENT DOCUMENTS 4,424,575 A * 1/1984 Clarke et al. .................. 715/201
5,557,722 A * 9/1996 DeRose et al. ................ 715/234

(Continued)

FOREIGN PATENT DOCUMENTS

JP 11-213011 8/1999
WO WO 2007/116204 10/2007

OTHER PUBLICATIONS

Hatzivassiloglou, Vasileios, et al, "SIMFINDER: A Flexible Clustering Tool for Text Summarization", 2001, Proceedings of the NAACL Workshop on Automatic Summarization, Dept. of Computer Science, Columbia University, pp. 1-9.*

(Continued)

*Primary Examiner* — Laurie Ries

(57) ABSTRACT

Disclosed is a computer-implemented method of presenting data which has been automatically extracted from a digital representation of a document to a curator for review, the extracted data comprising annotation entity data concerning one or more instances of entities which have been identified in the digital representation of a document, the annotation entity data comprising data specifying the location of the identified instances of entities within the digital representation of a document, the method comprising the steps of (i) displaying in a first region of a display screen a user selectable portion of the digital representation of a document with said instances of entities which are specified by the annotation entity data as being located within the displayed portion of the digital representation of a document highlighted at the location specified by the annotation entity data; (ii) displaying in a second region of the display screen a list of a plurality of instances of entities which have been identified in the digital representation of a document, at least one of the listed instances of an entity having a user selectable user interface element associated therewith; and (iii) responsive to a user selecting the user selectable user interface element associated with an instance of an entity, adjusting the portion of the digital representation of a document which is displayed in the first region to include the location within the digital representation of a document where the instance of an entity associated with the selected user interface element is located.

14 Claims, 18 Drawing Sheets

U.S. PATENT DOCUMENTS

| | | | |
|---|---|---|---|
| 5,745,113 A * | 4/1998 | Jordan et al. | 715/835 |
| 5,838,313 A * | 11/1998 | Hou et al. | 715/201 |
| 6,457,026 B1 | 9/2002 | Graham et al. | |
| 2004/0261016 A1 * | 12/2004 | Glass et al. | 715/512 |
| 2005/0131649 A1 | 6/2005 | Larsen et al. | |
| 2006/0041538 A1 * | 2/2006 | King et al. | 707/3 |
| 2006/0048058 A1 * | 3/2006 | O'Neal et al. | 715/730 |
| 2006/0129606 A1 * | 6/2006 | Horvitz et al. | 707/104.1 |
| 2006/0143559 A1 * | 6/2006 | Spielberg et al. | 715/512 |
| 2006/0218171 A1 * | 9/2006 | Wakeam et al. | 707/101 |
| 2006/0242192 A1 * | 10/2006 | Musgrove et al. | 707/102 |
| 2006/0262976 A1 * | 11/2006 | Hart et al. | 382/190 |
| 2006/0294094 A1 * | 12/2006 | King et al. | 707/6 |
| 2007/0033221 A1 * | 2/2007 | Copperman et al. | 707/103 R |
| 2007/0038610 A1 * | 2/2007 | Omoigui | 707/3 |
| 2007/0044010 A1 * | 2/2007 | Sull et al. | 715/500.1 |
| 2007/0050411 A1 * | 3/2007 | Hull et al. | 707/104.1 |
| 2007/0192140 A1 * | 8/2007 | Gropper | 705/3 |
| 2007/0204211 A1 * | 8/2007 | Paxson | 715/501.1 |
| 2008/0021880 A1 | 1/2008 | Ren et al. | |
| 2008/0065685 A1 * | 3/2008 | Frank | 707/102 |

OTHER PUBLICATIONS

International Search Report for PCT/GB2008/050959, mailed May 26, 2009.

Written Opinion of the International Searching Authority for PCT/GB2008/050959, mailed May 26, 2009.

Wright "How to Index Online", Indexer Soc. Indexers UK, [online] vol. 20, No. 3, Apr. 1997, pp. 115-120, XP002526922.

Office Action (3 pgs.) dated Jan. 8, 2013 issued in corresponding Japanese Application No. 2010-529460 with an at least partial English-language translation thereof (5 pgs.).

* cited by examiner

Glycogen synthase kinase3 beta phosphorylates serine 33 of p53 and activates p53's transcriptional activity BACKGROUND: The p53 protein is activated by genotoxic stress, oncogene expression and during senescence, p53 transcriptionally activates genes involved in growth arrest and apoptosis. p53 activation is regulated by post-translational modification, including phosphorylation of the N-terminal transactivation domain. Here, we have examined how Glycogen Synthase Kinase (GSK3), a protein kinase involved in tumorigenesis, differentiation and apoptosis, phosphorylates and regulates p53. RESULTS: The 2 isoforms of GSK3, GSK3alpha and GSK3beta, phosphorylate the sequence Ser-X-X-X-Ser(P) when the C-terminal serine residue is already phosphorylated. Several p53 kinases were examined for their ability to create GSK3 phosphorylation sites on the p53 protein. Our results demonstrate that phosphorylation of serine 37 of p53 by DNA-PK creates a site for GSK3beta phosphorylation at serine 33 in vitro. GSK3alpha did not phosphorylate p53 under any condition. GSK3beta increased the transcriptional activity of the p53 protein in vivo. Mutation of either serine 33 or serine 37 of p53 to alanine blocked the ability of GSK3beta to regulate p53 transcriptional activity. GSK3beta is therefore able to regulate p53 function in vivo. p53's transcriptional activity is commonly increased by DNA damage. However, GSK3beta kinase activity was inhibited in response to DNA damage, suggesting that GSK3beta regulation of p53 is not involved in the p53-DNA damage response. CONCLUSIONS: GSK3beta can regulate p53's transcriptional activity by phosphorylating serine 33. However, GSK3beta does not appear to be part of the p53-DNA damage response pathway. Instead, GSK3beta may provide the link between p53 and non-DNA damage mechanisms for p53 activation.

FIG. 6

```xml
<?xml version="1.0" encoding="UTF-8" ?>
<document>
<meta>
<attr name="abstract_from">pubmed</attr>
<attr name="abstract_or_fulltext">abstract</attr>
<attr name="pubmed_central_id">35361</attr>
<attr name="search_parameters">Apoptosis, ubiquitination, Phosphorylation, Cell cycle</attr>
<attr name="url">http://www.ncbi.nlm.nih.gov/entrez/query.fcgi?term=35361&search=Find+Articles&db=pmc&cmd=search&pmfilter_Fulltext=on&pmfilter_Relevance=on</attr>
</meta>
<text>
<title>Glycogen synthase kinase3 beta phosphorylates serine 33 of p53 and activates p53's transcriptional activity</title>
<body>BACKGROUND: The p53 protein is activated by genotoxic stress, oncogene expression and during senescence, p53 transcriptionally activates genes involved in growth arrest and apoptosis. p53 activation is regulated by post-translational modification, including phosphorylation of the N-terminal transactivation domain. Here, we have examined how Glycogen Synthase Kinase (GSK3), a protein kinase involved in tumorigenesis, differentiation and apoptosis, phosphorylates and regulates p53. RESULTS: The 2 isoforms of GSK3, GSK3alpha and GSK3beta, phosphorylate the sequence Ser-X-X-X-Ser(P) when the C-terminal serine residue is already phosphorylated. Several p53 kinases were examined for their ability to create GSK3 phosphorylation sites on the p53 protein. Our results demonstrate that phosphorylation of serine 37 of p53 by DNA-PK creates a site for GSK3beta phosphorylation at serine 33 in vitro. GSK3alpha did not phosphorylate p53 under any condition. GSK3beta increased the transcriptional activity of the p53 protein in vivo. Mutation of either serine 33 or serine 37 of p53 to alanine blocked the ability of GSK3beta to regulate p53 transcriptional activity. GSK3beta is therefore able to regulate p53 function in vivo. p53's transcriptional activity is commonly increased by DNA damage. However, GSK3beta kinase activity was inhibited in response to DNA damage, suggesting that GSK3beta regulation of p53 is not involved in the p53-DNA damage response. CONCLUSIONS: GSK3beta can regulate p53's transcriptional activity by phosphorylating serine 33. However, GSK3beta does not appear to be part of the p53-DNA damage response pathway. Instead, GSK3beta may provide the link between p53 and non-DNA damage mechanisms for p53 activation.</body>
</text>
</document>
```

FIG. 7

```
                                  202              204
<?xml version="1.0" encoding="UTF-8"?>
<!DOCTYPE document PUBLIC "-//LTG-Cognia-ITI//DTD IE OUTPUT V1//EN" "ie-
output.dtd">
<document><meta><attr name="abstract_from">pubmed</attr><attr
name="abstract_or_fulltext">abstract</attr><attr          206
name="pubmed_central_id">35361</attr><attr
name="search_parameters">Apoptosis, ubiquitination, Phosphorylation,
Cell cycle</attr><attr
name="url">http://www.ncbi.nlm.nih.gov/entrez/query.fcgi?term=35361&
search=Find+Articles&db=pmc&cmd=search&pmfilter_Fulltext=on&
amp;pmfilter_Relevance=on</attr><attr                                       200
name="tokeniser_version">20050908</attr></meta><text><title>
<s><ent id="e1" type="protein" conf="100"
norm="http://www.cognia.com/txm/biomedical/#protein_P00493973"><w>Glycog
en</w> <w>synthase</w> <w>kinase3</w> <w>beta</w></ent>
<w>phosphorylates</w> <w>serine</w> <w>33</w> <w>of</w> <ent id="e2"     200
type="protein" conf="100"
norm="http://www.cognia.com/txm/biomedical/#protein_P00502885"><w>p53</w
></ent> <w>and</w> <w>activates</w> <ent id="e3" type="protein"         200
conf="100"
norm="http://www.cognia.com/txm/biomedical/#protein_P00502885"><w>p53</w 200
></ent><w>'s</w> <w>transcriptional</w> <w>activity</w></s>
</title><body>
<p><s><w>BACKGROUND</w><w>:</w> <w>The</w> <ent id="e4" type="protein"
conf="100"
norm="http://www.cognia.com/txm/biomedical/#protein_P00502885"><w>p53</w
></ent> <w>protein</w> <w>is</w> <w>activated</w> <w>by</w>
<w>genotoxic</w> <w>stress</w><w>,</w> <w>oncogene</w> <w>expression</w>
<w>and</w> <w>during</w> <w>senescence</w><w>,</w> <ent id="e5"
type="protein" conf="100"
norm="http://www.cognia.com/txm/biomedical/#protein_P00502885"><w>p53</w
></ent> <w>transcriptionally</w> <w>activates</w> <w>genes</w>
<w>involved</w> <w>in</w> <w>growth</w> <w>arrest</w> <w>and</w>
<w>apoptosis</w><w>.</w> <ent id="e6" type="protein" conf="100"
norm="http://www.cognia.com/txm/biomedical/#protein_P00502885"><w>p53</w
></ent> <w>activation</w> <w>is</w> <w>regulated</w> <w>by</w>
<w>post</w><w>-</w><w>translational</w> <w>modification</w><w>,</w>
<w>including</w> <w>phosphorylation</w> <w>of</w> <w>the</w>
<w>N</w><w>-</w><w>terminal</w> <w>transactivation</w>
<w>domain</w><w>.</w></s> <s><w>Here</w><w>,</w> <w>we</w> <w>have</w>
<w>examined</w> <w>how</w> <ent id="e7" type="protein" conf="100"
norm="http://www.cognia.com/txm/biomedical/#protein_P00696969"><w>Glycog
en</w> <w>Synthase</w> <w>Kinase</w></ent> <w>(</w><ent id="e8"
type="protein" conf="25.000"
norm="http://www.cognia.com/txm/biomedical/#protein_P00532669"><w>GSK3</
w></ent><w>)</w><w>,</w> <w>a</w> <w>protein</w> <w>kinase</w>
<w>involved</w> <w>in</w> <w>tumorigenesis</w><w>,</w>
<w>differentiation</w> <w>and</w> <w>apoptosis</w><w>,</w>
<w>phosphorylates</w> <w>and</w> <w>regulates</w> <ent id="e9"
type="protein" conf="100"
norm="http://www.cognia.com/txm/biomedical/#protein_P00502885"><w>p53</w
></ent><w>.</w></s> <s><w>RESULTS</w><w>:</w> <w>The</w> <w>2</w>
<w>isoforms</w> <w>of</w> <ent id="e10" type="protein" conf="25.000"
norm="http://www.cognia.com/txm/biomedical/#protein_P00532669"><w>GSK3</
w></ent><w>,</w> <ent id="e11" type="protein" conf="0"
norm="CD"><w>GSK3alpha</w></ent> <w>and</w> <ent id="e12" type="protein"
conf="100"
norm="http://www.cognia.com/txm/biomedical/#protein_P00733182"><w>GSK3be
ta</w></ent><w>,</w> <w>phosphorylate</w> <w>the</w> <w>sequence</w>
<w>Ser</w><w>-</w><w>X</w><w>-</w><w>X</w><w>-</w><w>X</w><w>-
</w><w>Ser(P)</w> <w>when</w> <w>the</w> <w>C</w><w>-</w><w>terminal</w>
<w>serine</w> <w>residue</w> <w>is</w> <w>already</w>
```

FIG. 8A

```
<w>phosphorylated</w><w>.</w></s> <s><w>Several</w> <ent id="e13"
type="protein" conf="100"
norm="http://www.cognia.com/txm/biomedical/#protein_P00502885"><w>p53</w
></ent> <w>kinases</w> <w>were</w> <w>examined</w> <w>for</w>
<w>their</w> <w>ability</w> <w>to</w> <w>create</w> <ent id="e14"
type="protein" conf="25.000"
norm="http://www.cognia.com/txm/biomedical/#protein_P00532669"><w>GSK3<//
w></ent> <w>phosphorylation</w> <w>sites</w> <w>on</w> <w>the</w> <ent
id="e15" type="protein" conf="100"
norm="http://www.cognia.com/txm/biomedical/#protein_P00502885"><w>p53</w
></ent> <w>protein</w><w>.</w></s> <s><w>Our</w> <w>results</w>
<w>demonstrate</w> <w>that</w> <w>phosphorylation</w> <w>of</w>
<w>serine</w> <w>37</w> <w>of</w> <ent id="e16" type="protein"
conf="100"
norm="http://www.cognia.com/txm/biomedical/#protein_P00502885"><w>p53</w
></ent> <w>by</w> <ent id="e17" type="protein" conf="100"
norm="http://www.cognia.com/txm/biomedical/#protein_P00519047"><w>DNA</w
><w>-</w><w>PK</w></ent> <w>creates</w> <w>a</w> <w>site</w> <w>for</w>
<ent id="e18" type="protein" conf="100"
norm="http://www.cognia.com/txm/biomedical/#protein_P00733182"><w>GSK3be
ta</w></ent> <w>phosphorylation</w> <w>at</w> <w>serine</w> <w>33</w>
<w>in</w> <w>vitro</w><w>.</w></s> <s><ent id="e19" type="protein"
conf="0" norm="CD"><w>GSK3alpha</w></ent> <w>did</w> <w>not</w>
<w>phosphorylate</w> <ent id="e20" type="protein" conf="100"
norm="http://www.cognia.com/txm/biomedical/#protein_P00502885"><w>p53</w
></ent> <w>under</w> <w>any</w> <w>condition</w><w>.</w></s> <s><ent
id="e21" type="protein" conf="100"
norm="http://www.cognia.com/txm/biomedical/#protein_P00733182"><w>GSK3be
ta</w></ent> <w>increased</w> <w>the</w> <w>transcriptional</w>
<w>activity</w> <w>of</w> <w>the</w> <ent id="e22" type="protein"
conf="100"
norm="http://www.cognia.com/txm/biomedical/#protein_P00502885"><w>p53</w
></ent> <w>protein</w> <w>in</w> <w>vivo</w><w>.</w></s>
<s><w>Mutation</w> <w>of</w> <w>either</w> <w>serine</w> <w>33</w>
<w>or</w> <w>serine</w> <w>37</w> <w>of</w> <ent id="e23" type="protein"
conf="100"
norm="http://www.cognia.com/txm/biomedical/#protein_P00502885"><w>p53</w
></ent> <w>to</w> <w>alanine</w> <w>blocked</w> <w>the</w>
<w>ability</w> <w>of</w> <ent id="e24" type="protein" conf="100"
norm="http://www.cognia.com/txm/biomedical/#protein_P00733182"><w>GSK3be
ta</w></ent> <w>to</w> <w>regulate</w> <ent id="e25" type="protein"
conf="100"
norm="http://www.cognia.com/txm/biomedical/#protein_P00502885"><w>p53</w
></ent> <w>transcriptional</w> <w>activity</w><w>.</w></s> <s><ent
id="e26" type="protein" conf="100"
norm="http://www.cognia.com/txm/biomedical/#protein_P00733182"><w>GSK3be
ta</w></ent> <w>is</w> <w>therefore</w> <w>able</w> <w>to</w>
<w>regulate</w> <ent id="e27" type="protein" conf="100"
norm="http://www.cognia.com/txm/biomedical/#protein_P00502885"><w>p53</w
></ent> <w>function</w> <w>in</w> <w>vivo</w><w>.</w> <ent id="e28"
type="protein" conf="100"
norm="http://www.cognia.com/txm/biomedical/#protein_P00502885"><w>p53</w
></ent><w>'s</w> <w>transcriptional</w> <w>activity</w> <w>is</w>
<w>commonly</w> <w>increased</w> <w>by</w> <w>DNA</w>
<w>damage</w><w>.</w></s> <s><w>However</w><w>,</w> <ent id="e29"
type="protein" conf="100"
norm="http://www.cognia.com/txm/biomedical/#protein_P00733182"><w>GSK3be
ta</w></ent> <w>kinase</w> <w>activity</w> <w>was</w> <w>inhibited</w>
<w>in</w> <w>response</w> <w>to</w> <w>DNA</w> <w>damage</w><w>,</w>
<w>suggesting</w> <w>that</w> <ent id="e30" type="protein" conf="100"
norm="http://www.cognia.com/txm/biomedical/#protein_P00733182"><w>GSK3be
ta</w></ent> <w>regulation</w> <w>of</w> <ent id="e31" type="protein"
conf="100"
```

FIG. 8B

```
norm="http://www.cognia.com/txm/biomedical/#protein_P00502885"><w>p53</w
></ent> <w>is</w> <w>not</w> <w>involved</w> <w>in</w> <w>the</w> <ent
id="e32" type="protein" conf="100"
norm="http://www.cognia.com/txm/biomedical/#protein_P00502885"><w>p53</w
></ent><w>-</w><w>DNA</w> <w>damage</w> <w>response</w><w>.</w></s>
<s><w>CONCLUSIONS</w><w>:</w> <ent id="e33" type="protein" conf="100"
norm="http://www.cognia.com/txm/biomedical/#protein_P00733182"><w>GSK3be
ta</w></ent> <w>can</w> <w>regulate</w> <ent id="e34" type="protein"
conf="100"
norm="http://www.cognia.com/txm/biomedical/#protein_P00502885"><w>p53</w
></ent><w>'s</w> <w>transcriptional</w> <w>activity</w> <w>by</w>
<w>phosphorylating</w> <w>serine</w> <w>33</w><w>.</w></s>
<s><w>However</w><w>,</w> <ent id="e35" type="protein" conf="100"
norm="http://www.cognia.com/txm/biomedical/#protein_P00733182"><w>GSK3be
ta</w></ent> <w>does</w> <w>not</w> <w>appear</w> <w>to</w> <w>be</w>
<w>part</w> <w>of</w> <w>the</w> <ent id="e36" type="protein" conf="100"
norm="http://www.cognia.com/txm/biomedical/#protein_P00502885"><w>p53</w
></ent><w>-</w><w>DNA</w> <w>damage</w> <w>response</w>
<w>pathway</w><w>.</w></s> <s><w>Instead</w><w>,</w> <ent id="e37"
type="protein" conf="100"
norm="http://www.cognia.com/txm/biomedical/#protein_P00733182"><w>GSK3be
ta</w></ent> <w>may</w> <w>provide</w> <w>the</w> <w>link</w>
<w>between</w> <ent id="e38" type="protein" conf="100"
norm="http://www.cognia.com/txm/biomedical/#protein_P00502885"><w>p53</w
></ent> <w>and</w> <w>non</w><w>-</w><w>DNA</w> <w>damage</w>
<w>mechanisms</w> <w>for</w> <ent id="e39" type="protein" conf="100"
norm="http://www.cognia.com/txm/biomedical/#protein_P00502885"><w>p53</w
></ent> <w>activation</w><w>.</w></s></p>
</body><relations>
 <relation id="r1" conf="67.741425" norm="P00493973 - P00502885"
type="ppi">
   <argument ref="e1"/>
   <argument ref="e2"/>
 </relation>
 <relation id="r2" conf="42.08819" norm="P00493973 - P00502885"
type="ppi">
   <argument ref="e1"/>
   <argument ref="e3"/>
 </relation>
 <relation id="r3" conf="37.601925" norm="P00502885 - P00502885"
type="ppi">
   <argument ref="e4"/>
   <argument ref="e5"/>
 </relation>
 <relation id="r4" conf="33.473854" norm="P00696969 - P00502885"
type="ppi">
   <argument ref="e7"/>
   <argument ref="e9"/>
 </relation>
 <relation id="r5" conf="25.957853" norm="P00532669 - P00502885"
type="ppi">
   <argument ref="e8"/>
   <argument ref="e9"/>
 </relation>
 <relation id="r6" conf="29.081007" norm="P00532669 - P00502885"
type="ppi">
   <argument ref="e14"/>
   <argument ref="e15"/>
 </relation>
 <relation id="r7" conf="71.28724" norm="P00502885 - P00519047"
type="ppi">
   <argument ref="e16"/>
   <argument ref="e17"/>
 </relation>
```

FIG. 8C

```
<relation id="r8" conf="76.76192" norm="P00733182 - P00502885"
type="ppi">
  <argument ref="e21"/>
  <argument ref="e22"/>
</relation>
<relation id="r9" conf="26.230299" norm="P00502885 - P00733182"
type="ppi">
  <argument ref="e23"/>
  <argument ref="e24"/>
</relation>
<relation id="r10" conf="36.049717" norm="P00733182 - P00502885"
type="ppi">
  <argument ref="e24"/>
  <argument ref="e25"/>
</relation>
<relation id="r11" conf="57.14778" norm="P00733182 - P00502885"
type="ppi">
  <argument ref="e26"/>
  <argument ref="e27"/>
</relation>
<relation id="r12" conf="27.17637" norm="P00733182 - P00502885"
type="ppi">
  <argument ref="e29"/>
  <argument ref="e31"/>
</relation>
<relation id="r13" conf="54.6523" norm="P00733182 - P00502885"
type="ppi">
  <argument ref="e30"/>
  <argument ref="e31"/>
</relation>
<relation id="r14" conf="24.181108" norm="P00733182 - P00502885"
type="ppi">
  <argument ref="e33"/>
  <argument ref="e34"/>
</relation>
<relation id="r15" conf="24.375326" norm="P00502885 - P00502885"
type="ppi">
  <argument ref="e38"/>
  <argument ref="e39"/>
</relation>
</relations></text></document>
```

FIG. 8D

Glycogen synthase kinase3 beta phosphorylates serine 33 of p53 and activates p53's transcriptional activity BACKGROUND: The p53 protein is activated by genotoxic stress, oncogene expression and during senescence, p53 transcriptionally activates genes involved in growth arrest and apoptosis. p53 activation is regulated by post-translational modification, including phosphorylation of the N-terminal transactivation domain. Here, we have examined how Glycogen Synthase Kinase (GSK3), a protein kinase involved in tumorigenesis, differentiation and apoptosis, phosphorylates and regulates p53. RESULTS: The 2 isoforms of GSK3, GSK3alpha and GSK3beta, phosphorylate the sequence Ser-X-X-X-Ser(P) when the C-terminal serine residue is already phosphorylated. Several p53 kinases were examined for their ability to create GSK3 phosphorylation sites on the p53 protein. Our results demonstrate that phosphorylation of serine 37 of p53 by DNA-PK creates a site for GSK3beta phosphorylation at serine 33 in vitro. GSK3alpha did not phosphorylate p53 under any condition. GSK3beta increased the transcriptional activity of the p53 protein in vivo. Mutation of either serine 33 or serine 37 of p53 to alanine blocked the ability of GSK3beta to regulate p53 transcriptional activity. GSK3beta is therefore able to regulate p53 function in vivo. p53's transcriptional activity is commonly increased by DNA damage. However, GSK3beta kinase activity was inhibited in response to DNA damage, suggesting that GSK3beta regulation of p53 is not involved in the p53-DNA damage response. CONCLUSIONS: GSK3beta can regulate p53's transcriptional activity by phosphorylating serine 33. However, GSK3beta does not appear to be part of the p53-DNA damage response pathway. Instead, GSK3beta may provide the link between p53 and non-DNA damage mechanisms for p53 activation.

COMPUTER-IMPLEMENTED METHODS DISPLAYING, IN A FIRST PART, A DOCUMENT AND IN A SECOND PART, A SELECTED INDEX OF ENTITIES IDENTIFIED IN THE DOCUMENT

This application is the U.S. National Phase of international Application No. PCT/GB2008/050959, filed 17 Oct. 2008, which designated the U.S. and claims priority to Great Britain Application No(s). 0720304.5, filed 17 Oct. 2007 and 0803073.6, filed 20 Feb. 2008, the entire contents of each of which are hereby incorporated by reference.

FIELD OF THE INVENTION

The present invention relates to computer-implemented methods for providing a user interface which facilitates the curation of data which has been extracted from a digital representation of a document by an automatic information extraction procedure.

BACKGROUND TO THE INVENTION

The ever increasing volume of information produced by society and industry has led to ever increasing difficulties in storing, finding and analysing that information. Whereas there was a time when information, such as scientific and technical literature, could be adequately stored in printed form and indexed by hand, that time is now in the past and electronic storage, retrieval and analysis systems are an essential part of the modern world.

Some types of information processing can be adequately addressed by computerised analysis alone. For example, searchable directories of web pages can be automatically prepared without human intervention and used to store large volumes of information and to retrieve this information in response to queries, such as which web pages include specific words.

However, some information processing tasks cannot be automated, or cannot be automated to the standard which would be achieved by a human. For example, the accurate automatic analysis of documents comprising natural language text constitutes an especially difficult problem.

The automatic analysis of natural language text documents is addressed by the growing scientific field of natural language processing (NLP), also referred to as computational linguistics. NLP has been used to carry out tasks which previously required to be carried out by humans, but remains an imperfect science under continual development. Although it is often desirable to use automatic methods of analysing natural language, rather than human analysis, due to the cost and speed benefits of computerisation, there are many applications where human analysis remains essential.

One example of a field where there is a large volume of information, which would ideally be analysed automatically where possible, is the scientific literature, for example the biomedical scientific literature. In order to make new scientific discoveries and draw conclusions from existing data, it is desirable to be able to store and recall information concerning relations between biological entities which are mentioned in the scientific literature. For example, where a scientific paper provides evidence to support a hypothesis that a first protein interacts with a second protein in vivo, it is desirable to store that information in a searchable database. Such databases can be valuable aids to technical progress.

International Patent Application Publication Number WO 2005/017692 (Cognia Corporation) describes a relational database for use in biomedical research which includes information about entities (such as proteins, genes, compounds etc.) and interactions between these entities. Data concerning interactions is stored in the database along with references to scientific papers which provide evidence for the interactions. Thus, the database can be queried by users not just to find out information about entities and interactions between entities, but also to thereby identify relevant sources within the scientific literature. Data is entered into the database by human curators who read scientific literature, identify entities referred to in individual documents and relations which are hypothesized, discussed or proven by data within those documents. A computer-user interface is provided to curators which allows them to input data by selecting options via an ontology browser which, amongst other data, defines normalised forms for the names of entities. Thus, the data inputted by the curators uses standardised terms, which avoids entities being referred to by different names and thus improves the quality of the database.

However, a disadvantage of the system described in WO 2005/017692 is that it requires a substantial amount of time to be spent by skilled curators to compile the database, which can be costly.

PCT/GB2007/001170 (ITI Scotland Limited) discloses an information extraction procedure in which annotation data concerning instances of entities in a digital representation of a document, including the location of the instances of entities within the digital representation of a document, is automatically prepared by information extraction apparatus and presented to a human curator for review, using a computer-user interface. This arrangement reduces the time required by human curators to compile a database.

The present invention aims to provide an improved computer-user interface for use in reviewing data which has been automatically extracted from digital representations of documents by information extraction apparatus, for example, for use by a curator while reviewing data for export to a database.

SUMMARY OF THE INVENTION

According to a first aspect of the present invention there is provided a computer-implemented method of presenting extracted data which has been automatically extracted from a digital representation of a document to a curator for review, the extracted data comprising annotation entity data concerning one or more instances of entities which have been identified in the digital representation of a document, the annotation entity data comprising data specifying the location of the identified instances of entities within the digital representation of a document, the method comprising the steps of:
  (i) displaying in a first region of a display screen a user selectable portion of the digital representation of a document with said instances of entities which are specified by the annotation entity data as being located within the displayed portion of the digital representation of a document highlighted at the location specified by the annotation entity data;
  (ii) displaying in a second region of the display screen a list of a plurality of instances of entities which have been identified in the digital representation of a document, at least one of the listed instances of an entity having a user selectable user interface element associated therewith; and
  (iii) responsive to a user selecting the user selectable user interface element associated with an instance of an entity, adjusting the portion of the digital representation of a document which is displayed in the first region to include the location within the digital representation of a document where the instance of an entity associated with the selected user interface element is located.

The method enables a curator to more rapidly find the section of a digital representation of a document which they must study in order to review and, if necessary amend and/or input, annotation data concerning individual instances of entities when curating a digital representation of a document.

The list of a plurality of instances of entities which have been identified in the digital representation of a document may be a list which comprises or consists of automatically identified instances of entities, for example, the automatically identified instances of entities which the annotation entity data concerns.

The list of a plurality of instances of entities which have been identified in the digital representation of a document may be a list which comprises or consists of identified instances of entities which have been reviewed by a curator.

The list of a plurality of instances of entities which have been identified in the digital representation of a document may comprise instances of entities which were not specified in the extracted data but were identified by a curator.

The list of a plurality of instances of entities which have been identified in the digital representation of a document may comprise instances of entities in respect of which curated data records have been prepared for output to a database.

The method may comprise displaying a segment of text from the digital representation of a document, from around an individual instance of an entity, in the list of a plurality of instances of entities. The user selectable user interface element may comprise the segment of text concerning an individual instance of an entity, or a portion of the segment of text concerning an individual instance of an entity. For example, the user selectable user interface element may be highlighted text denoting the entity within a segment of text concerning the individual instance of an entity.

The step of adjusting the portion of the digital representation of a document which is displayed in the first region to include the location within the digital representation of a document where the instance of an entity associated with the selected user interface element is located may comprise adjusting the portion of the digital representation of a document which is displayed in the first region so that the instance of an entity associated with the selected user interface element is located within a specific portion of the first region, for example, generally half way up the first region.

Preferably, method further comprises highlighting instances of relations identified as being located within the portion of the digital representation of a document which is displayed in the first region at the identified location of the identified instances of relations, and the method further comprises displaying in a second region of the display screen a list of a plurality of instances of relations which have been identified in the digital representation of a document, at least one of the listed instances of an relation having a user selectable user interface element associated therewith; and responsive to a user selecting the user selectable user interface element associated with an instance of a relation, adjusting the portion of the digital representation of a document which is displayed in the first region to include the location within the digital representation of a document where the instance of a relation associated with the selected user interface element is located. The list of a plurality of instances of relations may be displayed at the same time, or a different time as the list of a plurality of instances of entities.

Preferably, the method further comprises providing a user with computer-user interface means (e.g. a computer-user interface) for reviewing extracted data concerning instances of entities (and optionally relations).

Preferably, the method further comprises providing a user with computer-user interface means (e.g. a computer-user interface) operable to receive new or amended data concerning instances of entities (and optionally relations) from a curator.

Preferably, the method further comprises providing a user with computer-user interface means (e.g. a computer-user interface) operable to receive data concerning instances of entities (and optionally relations) which have been identified within the digital representation of a document by a curator, but are not specified by the extracted data.

The method is typically carried out by computing apparatus in electronic communication with a display, for example a computer in electronic communication with a display. The or each user selectable user interface element is typically selectable with a pointing device associated with the computing apparatus, for example a mouse in electronic communication with said computer. The or each user selectable user interface element may be selectable by operating the pointing device to bring a move a pointer over a region of the display including the user interface element. For example, the or each user selectable user interface element may be selectable responsive to a "mouseover" event. The selection of the user selectable user interface element may, or may not, require a further user actuated selection event, such as clicking a mouse button.

The method may comprise the step of automatically extracting annotation entity data concerning instances of entities (and optionally annotation relation data), using information extraction apparatus, to prepare the extracted data for review.

The method may comprise carrying out a method according to the seventeenth aspect of the invention, and displaying a representation of user selected node elements from a group of node elements in the second region of the display, wherein one or more groups of leaf node elements associated with instances of entities, which are children of the same non-leaf node element, are displayed as the list of a plurality of instances of entities, and each leaf node element functions as, or comprises, a user selectable user interface element associated with an instance of an entity in the list of a plurality of instances of entities.

Further optional feature of the first aspect of the invention correspond to the features discussed below in relation to the first through sixteenth aspects of the invention.

According to a second aspect of the present invention there is provided a method of editing annotation data associated with a digital representation of a document, the method comprising the steps carried out by computing apparatus of:

(i) receiving as input data a digital representation of a document and annotation data, the annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of instances of entities comprise references to ontology data;

(ii) displaying in a first region of a display screen a user selectable portion of the digital representation of a document to a user of computer-user interface means (such as a computer-user interface), with annotations dependent on the annotation data, the said annotations including at least highlighting one or more of the instances of entities whose location is specified in the annotation entity data at the location within the digital representation of a document specified by the annotation entity data;

(iii) preparing amended annotation data responsive to instructions received from a user of the computer-user interface means; and (iv) outputting output data derived from the amended annotation data, wherein the method further comprises providing a user selectable operating mode in which the computer-user interface means is operable to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjusting the portion of the digital representation of a document which is displayed in the first region to include the location within the digital representation of a document where the instance of an entity associated with the selected user interface element is located.

The output data preferably comprises the amended annotation data.

In a preferred embodiment, the method of editing annotation data is part of a method of populating a database. Accordingly, the invention extends in a third aspect to a method of populating a database, the method comprising editing annotation data associated with a digital representation of a document by a method according to the first aspect of the present invention and populating the database with the output data. Within this description and the appended claims "editing annotation data" includes both amending annotation data such as to change the annotation data and preparing new annotation data or output data derived from new annotation data by amending annotation data or data derived therefrom.

Preferably, the annotation data is obtained by automatic computer analysis of the digital representation of a document.

Thus, in a fourth aspect, the invention also extends to a method of populating a database according to the third aspect of the invention, wherein the annotation data which is received as input data for the step of editing annotation data is obtained by the steps carried out by computing apparatus of receiving as input data a digital representation of a document, and analysing the digital representation of a document, identifying one or more instances of entities contained in the digital representation of the document and, for at least some of the identified instances of entities, storing annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to ontology data, and wherein the stored annotation data is used as input data for the step of editing annotation data.

The invention therefore provides a method for enabling a human curator to review and amend annotation data derived initially by the automatic analysis by computing apparatus of a digital representation of a document. The method will typically be repeated to allow the analysis and review of digital representations of a plurality of documents.

The process of storing data which specifies the location of an instance of an entity within a digital representation of a document, and the display to a user of computer-user interface means of at least part of the analysed digital representation of a document, with one or more of the identified instances of entities highlighted at the specified location within the digital representation of a document, facilitates a human curator in reviewing and checking the automatic analysis. We have found that providing annotations on a digital representation of a document facilitates a curator in identifying relevant features which require checking and curation and improves their speed of working in comparison to a system where a curator reads a printed document and enters data concerning entities, relations etc. using a computer-user interface such as that described in WO 2005/017692.

In certain embodiments, the display of annotations which are dependent on annotation data at the location within the digital representation of a document specified by the annotation data allows the human curator to add annotation data which cannot be accurately determined by computing alone. This facilitates the correction and review by a human curator of automatically prepared annotation data.

The step of preparing amended annotation data may comprise amending the annotation data. The step of preparing amended annotation data may further comprise interactively updating the display provided by the computer-user interface means. By enabling a curator to amend the annotation data, and by interactively updating the display provided by the computer-user means, the invention may allow the human curator to more conveniently add, amend or check annotation data which is dependent on the correct annotation of an entity, for example an annotation relating to a relation between two or more entities. The resulting annotation data which has been amended by this procedure is useful for the creation or amendment of an ontology database and/or for the preparation of training data for training a trainable information extraction module.

The step of preparing amended annotation data may comprise the step of displaying provisional amended annotation data derived from (e.g. copied from or extracted from) the annotation data and updating the provisional amended annotation data responsive to instructions received from a user of the computer-user interface means. The provisional amended annotation data may be derived from annotation data responsive to selection by a user of the displayed annotation which is dependent on the said annotation data. Thus, one or more interactive user-interface elements which are displayed to a user, such as a buttons, checks boxes, text entry fields, menus, drop-down menus etc., which represent provisional amended annotation data, may be automatically pre-populated using annotation data concerning a user-selected annotation and the user may be provided with the option to interactively amend the provisional amended annotation data and its representation by the one or more interactive user-interface elements, to prepare the amended annotation data. In this case, the annotation data which was received as input data may or may not be amended.

The output data may comprise output entity data concerning one or more entities, derived from the annotation entity data. The output entity data preferably comprises identifiers of one or more entities. Typically, the identifiers of entities are references to ontology data. The output data could include the location of one or more identified instances of entities within the document, but the output data may not include the location of the identified instances of entities within the digital representation of a document.

Preferably, the output data comprises a document identifier. This makes it possible for one or more documents containing information supporting data in the database to be identified.

Preferably, the annotation data comprises annotation relation data concerning instances of relations between entities described by the digital representation of the document. The step of preparing amended annotation data may comprise the step of receiving data concerning one or more instances of relations between entities from a user of the computer-user interface means and preparing amended annotation relation data accordingly.

The amended annotation data may be in a different format to the initial (i.e. received) annotation data, but the amended annotation data may be in the same format as the initial (i.e. received) annotation data. The optional and preferred features described herein in relation to the annotation data may be optional and preferred features of the amended annotation data and, where relevant, provisional amended annotation data, throughout the method, where applicable, unless stated otherwise. Accordingly, the provisional amended annotation data may comprise provisional amended annotation entity data and provisional amended annotation relation data.

Preferably, the output data comprises output relation data concerning one or more relations between entities, which relations are described by the document, the said data concerning one or more relations derived from the amended annotation data.

Output relation data may concern a specific instance of a reference in the document to a relation between entities mentioned in the document. A relation may concern a conclusion of a document as a whole, for example, the output relation data may concern a relation which is a subject of the document, a conclusion of the document, or a hypothesis discussed or supported by the document.

It may be that the annotation data does not initially comprise annotation relation data, but that the amended annotation data does, or may, comprise annotation relation data. Thus, annotation relation data may be included within the annotation data for the first time responsive to instructions received from a user of the computer-user interface means. Where the computer-user interface means is adapted to create and display provisional amended annotation data, the computer-user interface means may allow a user to amend the provisional amended annotation data to specify a relation between entities. For example, the user may be allowed to define one or more entities to which the relation relates.

The output relation data may comprise the location of one or more instances of a relation within the digital representation of the document. The annotation relation data may comprise the location of the relation within the digital representation of a document. The step of analysing the digital representation of a document may include identifying the location of one or more instances of relations within the digital representation of a document and storing relation data specifying the location of the one or more instances of relations within the annotation data. This step may be carried out with reference to the ontology data, which may comprise ontology data concerning relations. Optionally, the annotation relation data comprises the location of one or more instances of relations within the digital representation of the data, and the output data does not comprise the location of any instances of relations within the digital representation of the data.

The identification and storage of data specifying the location of an instance of an entity within a digital representation of a document facilitates the automatic identification of relations between entities within the digital representation of a document (in embodiments which automatically identify relations between entities).

This is because some relation extraction algorithms known in the art take into account the proximity of entities, or the words surrounding or between entities, when determining whether the document indicates that there is a relation between entities. The identification and storage of data specifying the instance of an entity within a digital representation of a document facilitates the provision of a computer-user interface feature enabling a user to select an entity for use in preparing amended annotation data concerning that entity or a relation concerning that entity, by pointing to the entity with a pointing device, such as a mouse.

Where the annotation data comprises annotation relation data, the method may include the step, carried out by computing apparatus, of identifying one or more instances of entities in a digital representation of a document, but not include the step, carried out by computing apparatus, of identifying instances of relations between identified entities. Thus, annotation relation data may be stored only responsively to the actions of a user of computer-user interface means. However, in a preferred embodiment, the step carried out by computing apparatus of analysing the digital representation of a document includes the step of automatically identifying instances of relations between entities and storing annotation data comprising annotation relation data concerning the identified instances of relations.

The output data may comprise data concerning relations (such as output relation data), but not data concerning entities (such as output entity data), or data concerning entities (such as output entity data) but not data concerning relations (such as output relation data), or both data concerning relations and data concerning entities (such as output relation data and output entity data).

The amendments to the annotation data responsive to instructions from a user of the computer-user interface means preferably comprise one or more of: deleting annotation entity data concerning an instance of an entity; amending annotation entity data concerning an instance of an entity, for example, by amending the data specifying the location of the said instance of an entity, or the identifier or an instance of an entity (for example, by adding or amending a reference to ontology data, such as by adding a reference to a normalised form of an entity or amending a reference to a normalised form of an entity to refer to a different normalised form of an entity); adding annotation entity data concerning an instance of an entity; deleting annotation relation data concerning an instance of a relation; amending annotation relation data concerning an instance of a relation; adding annotation relation data concerning an instance of a relation.

The annotation entity data and/or the output entity data may comprise properties of entities. The annotation relation data and/or the output relation data may comprise properties of relations.

Properties of entities may comprise one or more of: the state of an entity (e.g. whether an entity is phosphorylated) or the location of an entity (e.g. the location of an entity within a cell) or a property of an entity (e.g. the molecular weight of a protein) or a class within which the entity falls (e.g. G proteins) or a species or taxon within which the entity is classified (e.g. drosophila melanogaster or insecta). The output entity data may comprise properties of entities derived automatically from the digital representation of a document and the step of analysing the digital representation of a document may include the step carried out by computing apparatus of determining properties of entities. This step may be carried out with reference to ontology data and the ontology data may comprise data concerning properties of entities.

The output relation data may comprise properties of relations derived automatically from the digital representation of a document and the step of analysing the digital representation of a document may include the step carried out by computing apparatus of determining properties of relations. This step is preferably carried out with reference to ontology data and the ontology data may comprise data concerning properties of relations.

The amendments to the annotation entity data or provisional amended annotation entity data responsive to instructions from a user of the computer-user interface means may comprise the addition, deletion or amendment of data concerning properties of entities. The output entity data may comprise data concerning properties of entities derived from the annotation entity data.

The amendments to the annotation relation data or provisional amended annotation relation data responsive to instructions from a user of the computer-user interface means may comprise the addition, deletion or amendment of data concerning properties of the relations. The output relation data may comprise data concerning properties of relations derived from the annotation relation data.

In embodiments which allow a user to add or amend annotation entity data or provisional amended annotation data, it becomes possible for a user of the computer-user interface means (or an automatic process) to store annotation relation data concerning a relation between entities which were not identified, or were not correctly identified when the computing apparatus identified instances of entities within the digital representation of a document. The computer-user interface means may comprise user interface elements which enable a user to amend annotation relation data or provisional amended annotation data by correcting an erroneous automatic identification of an entity or to input the identifier of an unidentified entity or an entity which was identified but which was not correctly automatically identified as an entity which the relation concerns. Accordingly, this enables a curator to review and correct annotation relation data or provisional amended annotation relation data.

In a preferred embodiment, the annotation entity data concerns specific instances of an entity within the digital representation of a document, but the output data concerns the entity per se. For example, there might be five references to a single protein in a digital representation of a document (perhaps using more than one synonym of the protein), but the output data may concern the entity per se (for example, the output data may comprise a property of the entity per se) without reference to a specific instance of the entity within the digital representation of a document.

In a preferred embodiment, the annotation relation data concerns specific instances of a relation within the digital representation of a document, but the output relation data concerns the relation per se. For example, there might be four references to a relation between two proteins in a digital representation of a document (perhaps using more than one synonym of the protein), but the output data may concern the relation per se (for example, the output data may comprise a property of the relation between the two proteins per se) without reference to a specific instance of the relation within the digital representation of a document.

Where the document comprises biomedical information, the entities may comprise chemical species, oligonucleotides, oligopeptides, oligosaccharides, polynucleotides, polypeptides or polysaccharides, biochemical macromolecules, such as proteins or nucleic acids, subcellular components, such as organelles, cells, viruses or multicellular organisms. The entity may be a part of a larger entity, (e.g. a domain of a protein), or a combination of entities (e.g. a protein complex).

The entity identifier may be an alias of an identifier of the entity in the database which is to be populated with the data (e.g. an accession number of the entity in the database which is to be populated with data). The entity identifier may be resolvable to an identifier of the entity in the database and the method may comprise the step of resolving the entity identifier to determine an identifier of a corresponding entity in the database which is to be populated with data.

Preferably, the entity identifier is a reference to data, within ontology data, which concerns a particular entity. Preferably, the ontology data comprises synonyms of entities. The ontology data typically comprises normalised forms of entities. The method may comprise the step of retrieving a normalised synonym of an entity from ontology data using the entity identifier and including that normalised synonym of the entity in the data with which the database is populated. One skilled in the art will appreciate that the normalised synonym of an entity is a matter of choice and may be different in different ontologies.

The annotation relation data, and optionally the output relation data, preferably comprises identifiers of entities between which a relation has been identified, and may simply consist of identifiers of entities between which a relation has been identified. The identifiers could be identifiers of specific instances of entities (e.g. a code denoting a particular word which denotes an entitiy) within the digital representation of a document. Alternatively, they could be identifiers of entities which do not relate to a specific mention of an entity (e.g. a code denoting a particular protein).

The annotation relation data, and optionally the output relation data, may comprise the location of an instance of a relation within the text. For example, the annotation relation data and/or the output relation data may comprise an identifier of a character within the digital representation of a document where text relating to an instance of a relation begins, and also an identifier of a character within the digital representation of a document where text relating to an instance of a relation ends. However, it may be the case that the annotation relation data, and optionally the output relation data does not comprise the location of an instance of a relation. In some embodiments, the annotation relation data comprises the location of one or more instances of a relation, but the output relation data does not.

In a preferred embodiment, the annotation relation data comprises identifiers of particular instances of entities within the digital representation of a document. As the location of identified instances of entities is stored, the location of a relation could be considered as extending from one entity to another.

The annotation relation data may comprise identifiers of entities (for example, an identifier of an entity may be a reference to ontology data which comprises synonyms of entities). Preferably, the annotation relation data comprises identifiers of specific instances of entities, for example, a character offset or word identifier.

Typically, the relation between entities is a binary relation between two entities, although the relation between entities may be a relation between two or more entities. The relation between entities may be a technical relation. For example, where the entities are proteins, the relation may be a proven or hypothesized technical relation between proteins. For example, the relation may be that a protein interacts with another protein.

A relation may be directional, for example, annotation relation data and/or output relation data may specify the direction of an interaction (e.g. that a first protein acted on a second protein).

A relation may be hypothetical. A relation may be proposed. A relation may be explicitly stated in a document. A relation may be implied by a document. A relation may be a negative fact or hypothesis, for example, that two entities do not interact or that a document does not support a conclusion.

The annotation relation data, and optionally, the output relation data, may comprise the location of a relation within the digital representation of a document. The annotation relation data, and optionally the output relation data, may comprise a location within the digital representation of a document where text specifying that relation begins and ends. The location may be implied by the annotation relation data, and optionally the output relation data, specifying identifiers of two or more entities and the annotation data comprising data specifying the location of two or more identified instances of entities. It may be that the annotation relation data comprises the location of one or more relations within the digital representation of a document but the output data does not comprise the location of one or more relations within the digital representation of a document.

Where the method includes the step of displaying data concerning at least some of any identified relations, and the annotation data comprises the location of the said relations within the digital representation of the document, or data from which the location of the said relations within the digital representation of the document can be derived, the at least some of any identified relations may be displayed at the location within the digital representation of a document which has been stored as annotation data.

Preferably, the annotation relation data and/or the output relation data comprises fragments of text identifying the entities which the relation concerns. The fragments of text may correspond to fragments of the digital representation of a document. However, the fragments of text may comprise normalised forms of the entities which the relation concerns. The method may include the step of determining a normalised form of one or more entities which a relation concerns, with reference to the ontology data, and including that normalised form in the output relation data and/or the annotation relation data and/or the provisional amended annotation relation data.

The annotation entity data specifying the location of an identified instance of an entity within the digital representation of the document may comprise the location of the identified instance of an entity within the digital representation of the document (e.g. the data may comprise a number associated with the character where the instance of an entity starts, or a number which has been allocated to the particular word denoting the instance of the entity). However, the data specifying the location of the identified instance of an entity within the digital representation of the document may comprise data from which the location of the identified instance of an entity within the digital representation of the document may be calculated. Preferably, some or all of the entity data (for example, the identifier of an entity) is embedded inline within the digital representation of the document and it is the location of the entity data within the digital representation of the document which specifies the location of the entity within the digital representation of the document.

The digital representation of the document may comprise the annotation data. In a preferred embodiment, the digital representation of a document and the annotation data comprise or consist of data stored in the form of a file in a markup language with annotation data being stored in the form of tagged values within the file. For example, the digital representation of a document may be stored in the form of an XML file, the format of which corresponds to an XML standard as issued from time to time by the world wide web consortium (see www.w3.org/xml), for example, XML 1.0 or XML 1.1, with the annotation data included therein as tagged values.

Annotation relation data may be stored inline within a digital representation of the document, but preferably annotation relation data is stored in the form of standoff annotation, either within the same file as the digital representation of the document, or as a separate file.

Amended annotation data may be prepared by amending stored annotation data. The amended annotation data may be amended by storing different annotation data and using the different annotation data. Amended annotation data may be prepared by amending provisional annotation data derived initially from the annotation data.

The digital representation of a document preferably comprises data representing text. Preferably, the document comprises text. The digital representation of a document preferably comprises characters, where characters are units of information used for the organization, control, or representation of textual data. The digital representation of a document may comprise characters according to a recognised international character repertoire such as ASCII, ISO 646, or ISO/IEC 10646 (Unicode).

The document may be a text document, such as an academic paper, patent document, book chapter or book. However, the document may comprise images or speech. The document may be a printed document, such as a document published in a printed book or paper. The document may be in an electronic format, for example, the document may be published electronically, for example as a Portable Document Format (PDF) file. If the document is in an electronic format then the digital representation of the document may be the document, a copy of the document or a plain text representation of the document. However, the digital representation of the document is generally derived from the document. For example, a printed document may be scanned and analysed by optical character recognition software.

The digital representation of the document may comprise a representation of only part of the document. The digital representation may omit some features of the document, for example, one or more of images, superscripts, subscripts, page numbers, page titles etc. which are included in the document. The digital representation of the document may be obtained by electronic analysis of a document. The method may comprise the step of analysing a document to prepare the digital representation of a document. Preferably, the digital representation of a document is not prepared by removing mark-up from an XML file.

The document identifier preferably identifies the document. For example, the document identifier may comprise a reference to a scientific paper, or an identification code or accession numbers such as a Pubmed ID. However, the document identifier may also or instead identify the digital representation of the document, for example the document identifier may be an identifier of a digital representation of a document within a private collection of digital representations of documents. The annotation data may comprise a document identifier of a document and a document identifier of the digital representation of a document. The document identifier may identify part of the document, for example, the abstract of a document. Different parts of the same document (or digital representations thereof) may have different document identifiers. For example, the document identifier for the abstract of a document may be different to the document identifier for the body of the text of a document. The document identifier may comprise an identifier of a collection of documents.

The document may be a technical document, such as a scientific paper, technical description, or a record of an experiment. The document may comprise information relating to a specific technical field, for example one or more of biomedical information, astrophysical information, geographical information, geophysical information, mathematical information, engineering information, or physical sciences information, in any combination. The document may be a patent publication or comprise patent information. The method may be repeated with further documents from the same technical field to populate a database with data concerning one or more of the said technical fields, in any combination.

The method may include the step of retrieving digital representations of documents fulfilling one or more criteria. The annotation data may comprise some or all of the said criteria and the method may comprise the step of storing some or all of the said criteria in the annotation data. The method may include the step of storing the digital representation of a document in the form in which it was originally retrieved and providing means for the user of the user-interface means to display the original digital representation of a document.

The database is preferably a relational database although the database may be any type of database, for example an object-oriented database, an object-relational database or a flat-file database.

The database preferably comprises some, or preferably all, of data concerning entities, data concerning properties of entities, data concerning relations between entities and data concerning properties of relations between entities.

The computer-user interface means preferably comprises a display, such as a computer monitor with user-interface components displayed thereon. The computer-user interface means preferably comprises means for providing instructions, such as a keyboard and/or a pointing device (such as a computer mouse).

Instances of entities may be highlighted at the location within the digital representation of a document which is specified by annotation entity data by presenting the instance of the entity differently to surrounding text (for example, in a different colour, style and/or font). Instances of entities may be highlighted at the location within the digital representation of a document specified by annotation entity data by displaying them on a different background colour to surrounding text.

Instances of relations may be highlighted at the location within the digital representation of a document which is specified by annotation relation data by displaying the instance of the relation differently to surrounding text (for example, in a different colour, style and/or font). Instances of relations may be highlighted at the location within the digital representation of a document specified by annotation relation data by displaying them on a different background colour to surrounding text. Instances of relations may however be displayed to a user of computer-user interface means other than at a location within the digital representation of the document which describes that relation.

The computer-user interface means may comprise means for enabling a user to select one or more instances of entities and to selectively display at least part of the digital representation of a document with the said selected instances of entities being highlighted differently to other instances of entities or the only highlighted instance of an entity.

The computer-user interface means may comprise means for enabling a user to select one or more instances of relations and to selectively display at least part of the digital representation of a document with the said selected instances of relations being highlighted differently to other instances of relations or the only highlighted instance of a relation.

The computer-user interface means may comprise means for amending the annotation data responsive to instructions received from a user of the computer-user interface means, which amendments do not result in an amendment to what is displayed to a user. For example, the computer-user interface means may be adapted to allow a user to amend tokenisation, but this may not affect the display.

The computer-user interface means may be adapted to allow a user to select whether the database is to be populated with output data concerning a particular relation, and the step of populating the database with output data include the step of populating the database with data concerning only one or more relations which were selected. Preferably, the computer-user interface means is adapted to allow a user to select whether the database is to be populated with output data concerning a particular instance of a relation.

The computer-user interface means may be adapted to allow a user to select whether the database is to be populated with data concerning a particular entity, and the step of populating the database with output data include the step of determining whether to populate the database with data concerning selected entities. Preferably, the computer-user interface means is adapted to allow a user to select whether the database is to be populated with output data concerning a particular instance of an entity.

The computer-user interface means may be adapted to allow a user to positively select an entity for output and, where an entity has been selected by a user for output, data concerning that entity is stored in the database.

For example, the computer-user interface means may comprise a user-interface item (for example, a check box) which can be selected (for example, checked) to indicate that the database is to be populated with output data concerning an entity derived from annotation entity data concerning a particular instance of an entity.

The computer-user interface means may be adapted to allow a user to positively select a relation for output and, where a relation has been selected by a user for output, data concerning that relation is stored in the database.

For example, the computer-user interface means may comprise a user-interface item (for example, a check box) which can be selected (for example, checked) to indicate that the database is to be populated with output data concerning a relation derived from annotation relation data concerning a particular instances of a relation.

The computer-user interface means may be adapted to allow a user to positively select a document for output, and, where a document has been selected for output by a user, data concerning all entities and/or relations referred to in that document in respect of which annotation data has been stored, is stored in the database. Alternatively, where a document has been selected for output by a user, that document might be output without further data concerning the entities and/or relations referred to in that document.

The computer-user interface means may be adapted to allow a user to reject a document and, where a document has been rejected by a user, data concerning entities and/or relations identified in that document is not stored in the database.

Preferably, the method also includes the step of storing the amended annotation data or outputting the amended annotation data for storage. The annotation data can therefore be reviewed at a later stage or used for other purposes. Where the digital representation of the document comprises annotation data, the amended annotation data may be stored, or output as output data, by storing a file comprising both a digital representation of the document and that annotation data (e.g. as an XML file).

The ontology data may comprise a normalised form of an entity. A or each reference to ontology data may comprise a reference to a normalised form of an entity in the ontology data. The ontology data may be a hierarchial data structure specifying entities and relationships between those entities. The ontology data may be indexed by a field which identifies a normalised form of an entity and/or one or more synonyms of an entity. The ontology data may be stored in an ontology database. The ontology data may be stored in the database which is to be populated. The ontology data may be derived from the database which is to be populated.

The ontology data may further comprise attributes of relations.

Data concerning entities and/or relations in the database may be stored with reference to the ontology data. However, data concerning entities and/or relations in the database could be stored with reference to second ontology data and the step of populating the database may include the step of translating references to ontology data to refer to the second ontology data. The step of translating references to ontology data typically comprises translating identifiers of entities.

The computer-user interface means may be adapted to enable a user to amend the ontology data. The method may comprise the step of amending the ontology data responsive to instructions received through a user of the computer-user interface means.

The computer-user interface means may be adapted to enable a user to cause data concerning an entity to be added to the ontology data. The method may comprise the step of adding ontology data concerning an entity to the ontology data responsive to instructions received through a user of the computer-user interface means.

The computer-user interface means may be adapted to enable a user to cause data concerning a relation to be added to the ontology data. The method may comprise the step of adding ontology data concerning a relation to the ontology data responsive to instructions received through a user of the computer-user interface means.

Preferably, the method further comprises the step of using the ontology data which has been amended (or amendable) responsive to instructions received by the user of computer-user interface means for the analysis of further digital representations of documents.

Preferably, the analysis of a digital representation of a document is carried out by trainable information extraction module which is trainable using training data which comprises digital representations of documents and annotation data comprising the location of instances of entities (optionally and/or relations) in the documents and identifiers of the identified entities (optionally and/or relations), and the computer-user interface means is adapted to allow an analysed digital representation of a document and annotation data relating to entities (optionally and/or relations) referred to in the digital representation of the document to be selected by a user for use as training data for training the trainable information extraction module, and the method further includes the step of retraining the trainable information extraction module using data comprising the selected training data and using the retained trainable information extraction module in the analysis of further documents.

Preferably, the step of analysing the digital representation of a document comprises the steps of tokenisation (carried out by a tokenisation software module), named entity recognition (carried out by a named entity recognition software module) and term normalisation (carried out by a term normalisation module). The step of analysing the digital representation of a document preferably further comprises the step of relation extraction.

The step of term normalisation is preferably carried out with reference to the ontology data. The step of term normalisation preferably includes the step of storing annotation entity data comprising identifiers of instances of one or more entities which have been identified in the digital representation of a document wherein the identifiers of instances of entities are identifiers of entities in ontology data.

Typically, the trainable information extraction module comprises the named entity recognition software module. The named entity recognition software may be trainable using selected training data comprises curated, annotated digital representations of documents. The named entity recognition software module preferably uses a maximum entropy algorithm trained on training data comprising the selected training data.

Preferably, the computer-user interface means is adapted to allow a user to select a batch of digital representations of documents for analysis and then to sequentially and/or simultaneously display the batch of digital representations of documents and amend annotation data concerning the batch of digital representations of documents. A batch of digital representations of documents may fulfil the same search criteria. The batch of digital representations of documents may have been retrieved responsive to a single search request.

Further optional features of the second, third and fourth aspects of the invention correspond to the optional features of the first aspect.

According to a fifth aspect of the present invention, there is provided a method of populating a second database, the method comprising the steps of populating a first database by the method of the second, third or fourth aspect of the present invention, and exporting some or all of the data used to populate the first database from the first database to the second database.

The first and second databases may be in a different format and the step of exporting some or all of the said data may comprise the step of translating the format of the exported data.

The identifiers of entities (and/or relations) in the first database may refer to first ontology data and the identifier of entities (and/or relations) in the second database may refer to second ontology data and the step of exporting some or all of the said data may comprise the step of translating references to the first ontology data to references to the second ontology data.

The method may include the step of importing ontology data from the second ontology data into the first ontology data, converting the format of the ontology data if required, and using the imported ontology data during the analysis of further documents.

The method may comprise the step of populating a plurality of second databases, at least two of which comprise different ontology data and/or different identifiers of entities. At least two of the plurality of second databases may be in different formats and/or the ontology data which is referred to by identifiers stored in at least two of the plurality of second databases may be in different formats.

The method may further comprise the step of creating a further database by including within that database some or all of the output data with which the database was populated by the method of any one of the first four aspects of the invention, translating or converting that data into another format if need be.

According to a sixth aspect of the present invention there is provided a database populated according to the method of any one of the second, fourth or fifth aspects of the invention.

According to a seventh aspect of the present invention, there is provided a method of outputting data responsive to a search request, comprising the steps of populating a database using the method of the second, fourth or fifth aspects of the invention, receiving a search request, querying the database to retrieve data relevant to the search request and outputting the retrieved data.

The method may include the step of retrieving one or more digital representations of a document responsive to a search request, subsequently populating the database using the method of the third, fourth or fifth aspects of the invention, and subsequently outputting data comprising data concerning the said retrieved digital representations of documents.

The method may include the step of logging search requests and selecting further digital representations of documents for subsequent analysis, or retrieving further digital representations of documents which fulfil one or more said search requests for subsequent analysis.

The method may further comprise the step of including the retrieved data, or data derived from the retrieved data, within a file (such as a web page) and transmitting that file responsive to the search request.

According to a eighth aspect of the present invention, there is provided a method of creating or amending an ontology database comprising ontology data, comprising the steps carried out by computing apparatus of:
(i) receiving as input data a digital representation of a document;
(ii) analysing the digital representation of a document, identifying one or more instances of entities contained in the digital representation of the document and, for at least some of the identified instances of entities, storing annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to the ontology data;
(iii) displaying in a first region of a display screen a user selectable portion of the digital representation of a document to a user of computer-user interface means, with annotations dependent on the annotation data, the said annotations including at least highlighting one or more of the instances of entities whose location is specified in the annotation entity data at the location within the digital representation of a document specified by the annotation entity data;
(iv) providing the user of computer-user interface means with means to amend the ontology data;
(v) preparing amended annotation data responsive to instructions received from a user of the computer-user interface means;
(vi) amending the ontology data responsive to instructions received by a user of the computer-user interface means;

wherein the method further comprises providing a user selectable operating mode in which the computer-user interface means is operable to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjusting the portion of the digital representation of a document which is displayed in the first region to include the location within the digital representation of a document where the instance of an entity associated with the selected user interface element is located.

The step of amending the ontology data may comprise one or more of deleting ontology data, adding ontology data or amending ontology data. Steps (iv) to (vi) may take place in any order or concurrently.

The ontology data may comprise a normalised form of an entity. The ontology data may be a hierarchial data structure specifying entities and relationships between those entities. The ontology data may be indexed by a field which identifies a normalised form of an entity and/or one or more synonyms of an entity. The ontology data may comprise ontology data concerning relations.

The method may further comprise the step of creating an ontology database by including within that database some or all of the ontology data created or amended by the method of the present invention, optionally converting the format of that ontology data if need be.

The method may further comprise the step of outputting output data derived from the amended annotation data and/or populating a database with output data derived from the amended annotation data. Preferred and optional features correspond to those discussed in relation to the second, third and fourth aspects of the invention.

According to a ninth aspect of the present invention, there is provided ontology data obtained by the method of the eighth aspect of the present invention.

According to a tenth aspect of the present invention, there is provided a method of training a trainable information extraction module, comprising the steps carried out by computing apparatus of:
(i) receiving as input data a digital representation of a document;
(ii) analysing the digital representation of a document using the trainable information extraction module, the trainable information extraction module identifying one or more instances of entities contained in the digital representation of the document and, for at least some of the identified instances of entities, storing annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to ontology data;
(iii) displaying in a first region of a display screen a user selectable portion of the digital representation of a document to a user of computer-user interface means, with annotations dependent on the annotation data, the said annotations including at least highlighting one or more of the instances of entities whose location is specified in the annotation entity data at the location within the digital representation of a document specified by the annotation entity data;
(iv) preparing amended annotation data responsive to instructions received from a user of the computer-user interface means;
(v) providing a user of the computer-user interface means with means to select a digital representation of a document for use in training the trainable information extraction module;
(vi) periodically retraining the trainable information extraction module using training data comprising at least part of the selected digital representation of a document and the amended annotation data which concerns the selected digital representation of a document; and wherein the method further comprises providing a user selectable operating mode in which the computer-user interface means is operable to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjusting the portion of the digital representation of a document which is displayed in the first region to include the location within the digital representation of a document where the instance of an entity associated with the selected user interface element is located.

The user-interface means may be adapted to enable a user to select a portion of the digital representation of a document for use in retraining the information extraction module and that portion of the digital representation of a document may be used for retraining the information extraction module. Typically, the information extraction module will be retrained using only annotation data which has been received and, where required, amended by a curator. Steps (iii) to (v) may take place simultaneously or concurrently.

The trainable information extraction module may comprise a tokenisation module, a named entity recognition module, a term normalisation module and a relation extraction module. Typically, only the named entity recognition module is trainable, however other modules within the trainable information extraction module may be trainable.

The method may further comprise the step of outputting output data derived from the amended annotation data and/or populating a database with output data derived from the amended annotation data. Preferred and optional features correspond to those discussed in relation to the second, third and fourth aspects of the invention.

In a eleventh aspect, the invention provides an information extraction module trained by the method of the tenth aspect of the present invention.

The invention extends in an twelfth aspect to a system for editing annotation data associated with a digital representation of a document, the system comprising computer-user interface means (such as a computer-user interface) and output means (such as an output module);

wherein the computer-user interface means is operable to receive as input data a digital representation of a document and annotation data, the annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of instances of entities comprise references to ontology data;

and wherein the computer-user interface means is operable to display a user selectable portion of the digital representation of a document in a first region of a display screen to a user of the computer-user interface means, with annotations dependent on the annotation data, the said annotations including at least highlighting one or more of the instances of entities whose location is specified in the annotation entity data at the location within the digital representation of a document specified by the annotation entity data;

and wherein the computer-user interface means is operable to receive instructions from a user of the computer-user interface means and to prepare amended annotation data responsive to the received instructions;

and wherein the output means is operable to output output data derived from the amended annotation data;

wherein the computer-user interface means is operable, in a user selectable operating mode, to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjust the portion of the digital representation of a document which is displayed in the first region to include the location within the digital representation of a document where the instance of an entity associated with the selected user interface element is located.

Preferred and optional features of the system and the data which the system is adapted to process correspond to those discussed in relation to the second, third and fourth aspects of the present invention.

The invention extends in a thirteenth aspect to a system for populating a database, the system comprising computer-user interface means (such as a computer-user interface) and output means (such as an output module);

wherein the computer-user interface means is operable to receive as input data a digital representation of a document and annotation data, the annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of instances of entities comprise references to ontology data;

and wherein the computer-user interface means is operable to display a user selectable portion of the digital representation of a document in a first region of a display screen to a user of the computer-user interface means, with annotations dependent on the annotation data, the said annotations including at least highlighting one or more of the instances of entities whose location is specified in the annotation entity data at the location within the digital representation of a document specified by the annotation entity data;

and wherein the computer-user interface means is operable to receive instructions from a user of the computer-user interface means and to prepare amended annotation data responsive to the received instructions;

and wherein the output means is operable to populate the database with output data derived from the amended annotation data.

wherein the computer-user interface means is operable, in a user selectable operating mode, to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjust the portion of the digital representation of a document which is displayed in the first region to include the location within the digital representation of a document where the instance of an entity associated with the selected user interface element is located.

Preferably, the system further comprises analysis means (such as an analysis module) operable to analyse the digital representation of a document.

Preferred and optional features of the system and the data which the system is adapted to process correspond to those discussed in relation to the second, third and fourth aspects of the invention.

In a fourteenth aspect, the invention extends to a system for populating a database, the system comprising analysis means (such as an analysis module), computer-user interface means (such as a computer-user interface) and output means (such as an output module);

wherein the analysis means is operable to receive as input data a digital representation of a document and to analyse the digital representation of a document, identify one or more instances of entities contained in the digital representation of the document and, for at least some of the identified instances of entities, store annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to ontology data;

wherein the computer-user interface means is operable to receive as input data a digital representation of a document and the annotation data stored by the analysis means and to display a user selectable portion of the digital representation of a document in a first region of a display screen to a user of the computer-user interface means, with annotations dependent on the annotation data, the said annotations including at least highlighting one or more of the instances of entities whose location is specified in the annotation entity data at the location within the digital representation of a document specified by the annotation entity data;

wherein the computer-user interface means is operable to receive instructions from a user of the computer-user interface means and to prepare amended annotation data responsive to the received instructions;

and wherein the output means is operable to populate the database with output data derived from the amended annotation data; and wherein the computer-user interface means is operable, in a user selectable operating mode, to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjust the portion of the digital representation of a document which is displayed in the first region to include the location within the digital representation of a document where the instance of an entity associated with the selected user interface element is located.

Preferred and optional features of the system and the data which the system is adapted to process correspond to the preferred and optional features of the second, third and fourth aspects of the invention.

According to a fifteenth aspect of the present invention, there is provided a system for creating or amending an ontology database comprising ontology data, the system comprising analysis means (such as an analysis module), computer-user interface means (such as a computer-user interface) and output means (such as an output module);

wherein the analysis means is operable to receive as input data a digital representation of a document and to analyse the digital representation of a document, identify one or more instances of entities contained in the digital representation of the document and, for at least some of the identified instances of entities, store annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to the ontology data;

wherein the computer-user interface means is operable to receive as input data a digital representation of a document and the annotation data stored by the analysis means and to display a user selectable portion of the digital representation of a document in a first region of a display screen to a user of the computer-user interface means, with annotations dependent on the annotation data, the said annotations including at least highlighting one or more of the instances of entities whose location is specified in the annotation entity data at the location within the digital representation of a document specified by the annotation entity data;

wherein the computer-user interface means is operable to receive instructions from a user of the computer-user interface means and to prepare amended annotation data responsive to the received instructions;

wherein the computer-user interface means is operable to receive instructions from a user of the computer-user interface means to amend the ontology data and to amend the ontology data responsive to the received instructions;

and wherein the output means is operable to populate the database with output data derived from the amended annotation data.

wherein the computer-user interface means is operable, in a user selectable operating mode, to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjust the portion of the digital representation of a document which is displayed in the first region to include the location within the digital representation of a document where the instance of an entity associated with the selected user interface element is located.

Preferred and optional features of the system and the data which the system is adapted to process correspond to the preferred and optional features discussed in relation to the eighth aspect of the invention.

According to a sixteenth aspect, the invention extends to a system for training a trainable information extraction module, the system comprising analysis means (such as an analysis module), computer-user interface means (such as a computer-user interface) and output means (such as an output module);

wherein the analysis means comprises a trainable information extraction module which is operable to receive as input data a digital representation of a document and to analyse the digital representation of a document, identify one or more instances of entities contained in the digital representation of the document and, for at least some of the identified instances of entities, store annotation data comprising annotation entity data concerning one or more instances of entities which have been identified in the digital representation of a document, the annotation entity data comprising identifiers of instances of one or more entities which have been identified in the digital representation of a document and data specifying the location of the identified instances of entities within the digital representation of a document, wherein the identifiers of entities comprise references to ontology data;

wherein the computer-user interface means is operable to receive as input data a digital representation of a document and the annotation data stored by the analysis means and to display a user selectable portion of the digital representation of a document in a first region of a display screen to a user of the computer-user interface means, with annotations dependent on the annotation data, the said annotations including at least highlighting one or more of the instances of entities whose location is specified in the annotation entity data at the location within the digital representation of a document specified by the annotation entity data;

wherein the computer-user interface means is operable to receive instructions from a user of the computer-user interface means and to prepare amended annotation data responsive to the received instructions;

wherein the computer-user interface means comprises means for a user to select a digital representation of a document for use in training the trainable information extraction module;

wherein the output means is operable to populate the database with output data derived from the amended annotation data;

and wherein the system is operable to periodically retrain the trainable information extraction module using training data comprising at least part of the selected digital representation of a document and the amended annotation data which concerns the selected digital representation of a document; and wherein the computer-user interface means is operable, in a user selectable operating mode, to display in a second region of the display screen a list of a plurality of instances of entities which have been identified in the digital representation of a document, at least one of the listed instances of an entity having a user selectable user interface element associated therewith; and responsive to a user selecting the user selectable user interface element associated with an instance of an entity, adjust the portion of the digital representation of a document which is displayed in the first region to include the location within the digital representation of a document where the instance of an entity associated with the selected user interface element is located.

Preferred and optional features of the system and the data which the system is adapted to process correspond to the preferred and optional features discussed in relation to the tenth aspect of the invention.

According to a seventeenth aspect of the present invention there is provided a computer-implemented method of presenting data which has been automatically extracted from a digital representation of a document to a user, the automatically extracted data comprising data specifying instances of entities which have been automatically identified in the digital representation of a document, the instances of entities having one or more properties associated therewith, the method comprising:

displaying a representation of user selected node elements from a group of node elements, wherein each node element in the group of node elements has either or both a parent node element and one or more child node elements, forming a branching tree structure, at least two node elements in the group of node elements being leaf node elements which have no child node elements, the remaining node elements being non-leaf node elements which have at least one child node element, each represented non-leaf node element being user selectable to determine whether child node elements of the said represented non-leaf node element are represented;

characterised in that each leaf node element is associated with an instance of an entity specified by the automatically extracted data and each non-leaf node element is associated with a value of a property of instances of entities, and each leaf node element which is an ultimate child of the respective non-leaf node element is associated with an instance of an entity which has the same respective value of a property.

By an "ultimate child" we refer to a leaf node element which is reachable by selecting the child node element of a node element, selecting one of its child node elements and so forth until a leaf node element is reached.

Accordingly, the invention enables a user to conveniently and interactively view node elements associated with instances of entities which have been identified in the digital representation of a document, grouped according to the values of one or more properties, facilitating the curation process.

The leaf node elements are typically represented using a character string which is representative of the instance of an entity, for example a section of text consisting of, or including, the instance of an entity, within the digital representation of a document.

At least part of the digital representation of a document may be displayed in a first region of the display and the representation of the user selected node elements may be displayed in a second region of a display. Leaf node elements may comprise user selectable user interface elements which, when selected by a user, cause the instance of an entity which the respective leaf node element concerns to be highlighted in the digital representation of a document and/or the view of at least part of the digital representation of a document in the first region of the display to be amended to show the instance of an entity which the respective leaf node element concerns. Accordingly, the method may be a method according to first or second aspect of the invention wherein the representation of user selected node elements is displayed in the second region of the display and leaf node elements are represented in the form of one or more lists of the instance of entities which they are associated with.

Preferably, for at least the majority, and typically each, non-leaf node element which has non-leaf node elements as children, each child non-leaf node element is associated with a different value of the same property.

Preferably, the property in respect of which non-leaf node elements which are children of the same non-leaf node element have different values is the same for each non-leaf node element at at least one, and typically each, depth within the branching tree structure.

Preferably, at least some, and typically each non-leaf node element is represented by an image including a number corresponding to the number of ultimate children of that non-leaf node element. This enables a curator to rapidly appreciate the number of instances of entities which have a specified value, or values, of one or more properties.

Thus, each leaf node element is preferably associated with an instance of an entity which has values of properties associated with each node element which is above it in the tree structure. By a node element being "above" a leaf node element in the tree structure, we mean that it is a node element reachable by selecting the parent node element of a node element one or more times.

At least one property may be the location of the instance of an entity within the digital representation of a document. For example, the property may have possible values denoting the section of a digital representation of a document, such as abstract, experimental section, results section etc., where the instance of an entity is located. This enables a reviewer to obtain an overview of which sections of the digital representation of a document contain relatively many or relatively few instances of entities.

At least one property may be the type of the instance of an entity. For example, when the method is used in connection with biomedical literature, the property may have possible values such as protein, gene, experimental method, organism etc.

At least one property may be the surface form of an instance of an entity in the digital representation of a document. At least one property may be the canonical form of an instance of an entity. For example, instances of entities comprising the surface forms: Muscle Creatine Kinase, CKMM and CK-3 (each of which refers to the same protein) may each have the same parent node element.

Preferably, the properties having different values associated with different node elements which are children of the same parent node element, are determined by configuration parameters which may be different for different applications.

One or more of the properties having different values associated with different node elements may be the status of curation of instances of entities, for example, whether an instance of an entity has been curated by a human curator. The method may include moving a leaf node element to another location in the tree structure responsive to a change in the status of curation of the instance of an entity associated with the leaf node element.

Although the embodiments of the invention described with reference to the drawings comprise methods performed by computer apparatus, and also computing apparatus, the invention also extends to program instructions, particularly program instructions on or in a carrier, adapted for carrying out the processes of the invention or for causing a computer to perform as the computer apparatus of the invention. Programs may be in the form of source code, object code, a code intermediate source, such as in partially compiled form, or any other form suitable for use in the implementation of the processes according to the invention. The carrier may be any entity or device capable of carrying the program instructions.

For example, the carrier may comprise a storage medium, such as a ROM, for example a CD ROM or a semiconductor ROM, or a magnetic recording medium, for example a floppy disc or hard disc. Further, the carrier may be a transmissible carrier such as an electrical or optical signal which may be conveyed via electrical or optical cable or by radio or other means. When a program is embodied in a signal which may be conveyed directly by cable, the carrier may be constituted by such cable or other device or means.

The preferred and optional features discussed above are preferred and optional features of each aspect of the invention to which they are applicable. For the avoidance of doubt, the preferred and optional features of the second and third aspects of the invention correspond to the preferred and optional features discussed in relation to the fourth aspect of the invention, where applicable.

BRIEF DESCRIPTION OF THE DRAWINGS

The invention will be further described, by way of example only, with reference to the following drawings in which:

FIG. 6 is an example text suitable for analysis by the system;

FIG. 7 is an XML file concerning the example text before information extraction;

FIGS. 8A, 8B, 8C and 8D constitute successive portions of an XML file concerning the example text after information extraction;

FIG. 9 is the text of FIG. 6 with identified entities underlined and identified relations labelled;

FIG. 10 is a schematic diagram of a curation computer-user interface;

DETAILED DESCRIPTION OF AN EXAMPLE EMBODIMENT

Figure 1:
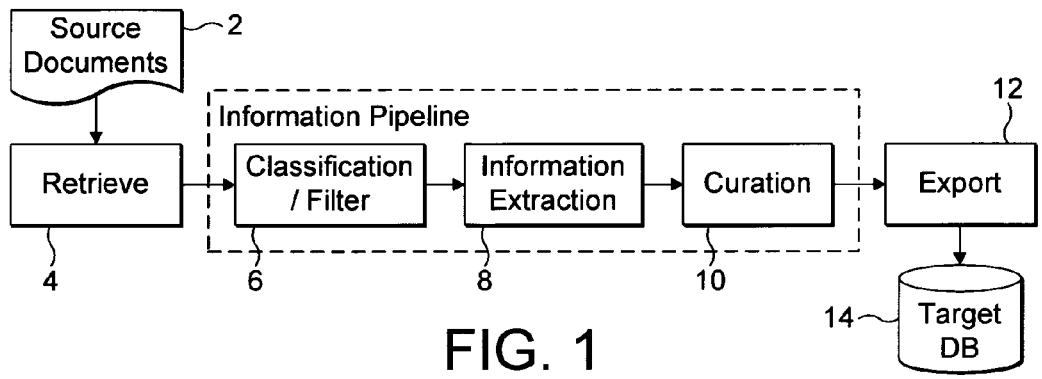
FIG. 1 is a schematic diagram of the main flow of information through a system according to the present invention.

By way of introduction, FIG. 1 is a schematic diagram of the main flow of information through an information extraction system according to the present invention. The example system extracts data from digital representations of biomedical text documents which include natural language text and presents the resulting extracted data to human curators for review. The example system is designed for the analysis of large number of digital representations of documents with extracted data being curated by a team of human curators.

Source documents 2 are retrieved 4 from a document source. The system analyses digital representations of documents and so the source documents will typically be digital representations of documents, for example, full text journal articles or Medline Abstracts, (Medline is a trade mark of the National Library of Medicine, Bethesda, Md.), although the documents may be retrieved in printed form and scanned. Document files (which constitute digital representations of documents) are then classified and filtered 6 before being subject to an information extraction procedure 8 using natural language processing (NLP) methods before being curated 10 by a human curator using a computer-user interface. Following the curation step, data is exported 12 to a target database 14. The flow of information through the system is discussed in more depth below.

Figure 2:
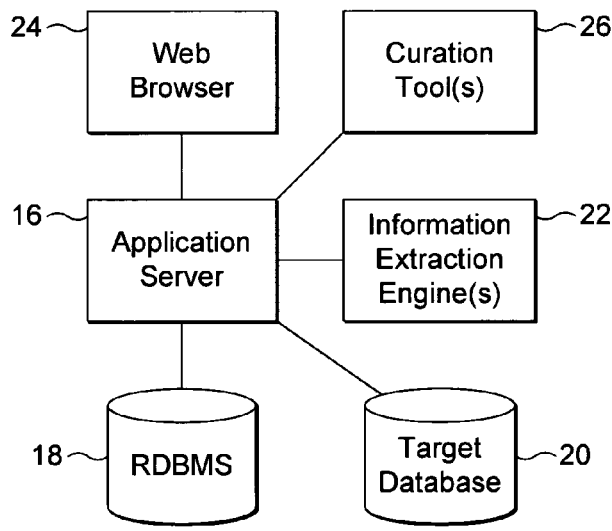
FIG. 2 is a schematic diagram of key components of the system.

FIG. 2 is a schematic diagram of key components of the system. Application logic running on an application server 16 controls the system via a set of core services running in a J2EE application server (J2EE is a trade mark of Sun Microsystems) using a Spring Framework container (The Spring Framework is an open source project described at www.springframework.org). Relevant data, such as document files (constituting digital representations of documents) is retrievably stored in the form of XML files by a relational database management system 18. Information extraction engine(s) 22 are implemented by a single processor or one or more processors operating in parallel. A web browser 24 provides administrative access to the system and control over the curation process. Curation tools 26 implement a computer-user interface on computers, each of which has a display, keyboard and a pointing device such as a mouse. Individual components can be connected through a network. The application server will typically communicate with web browsers and curation tools over SOAP and HTTP though an internet protocol network. One skilled in the art will recognise that several components of the system can be implemented on a single computer, or individual components may be implemented on a single computer or a cluster of computers.

Figure 3:
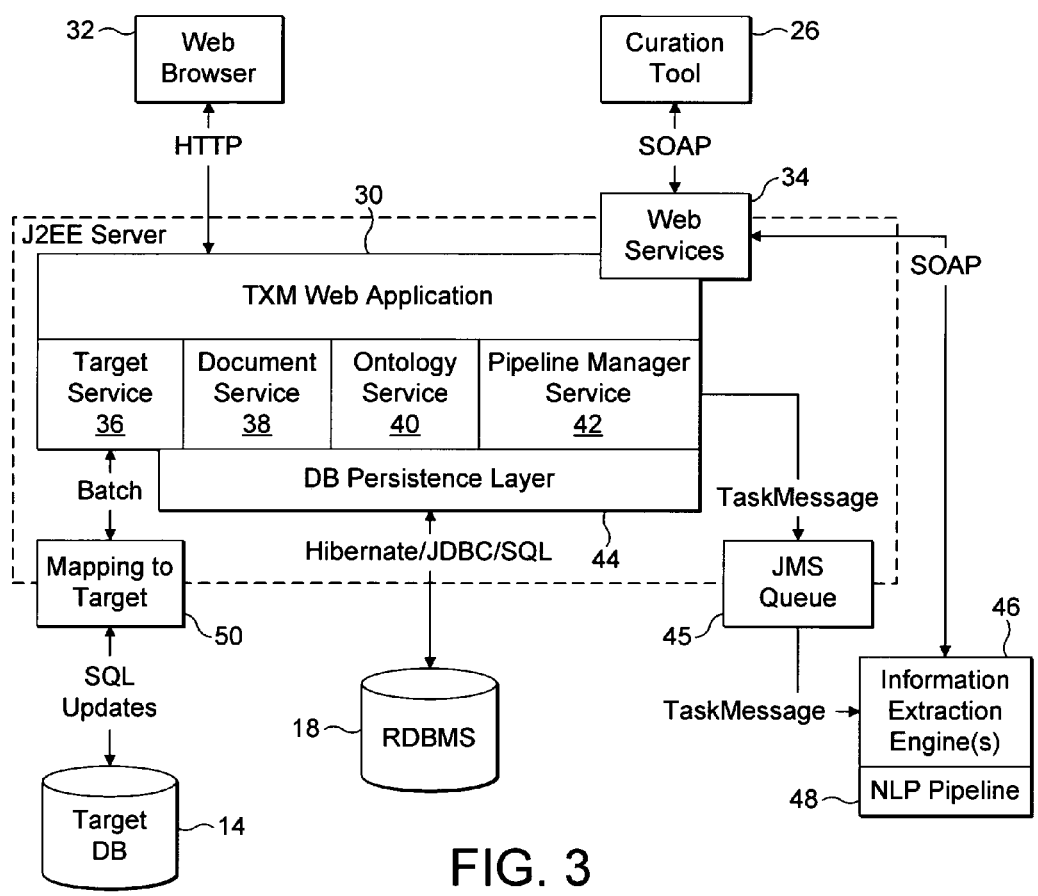
FIG. 3 is a schematic diagram of layers within the system architecture.

The software components which make up the system can be described in the form of layers, illustrated schematically in FIG. 3. Presentation logic is encapsulated in web application layer 30, allowing control of the system via a web browser 32. Web services components 34 communicate with one or more curation tools 26 delivered to web browsers as Java applications using Java Web Start. (Java and Java Web Start are trade marks of Sun Microsystems).

Key aspects of the application logic are encapsulated in four key services, namely a target service 36 which includes control logic relating to bidirectional communication with a target database 14, including logic relating to the export of output data for populating a target database; a document service 38 which serves as an API to collections of document files which have been gathered and stored, allowing other components of the system read/write access to the data in an abstracted and controlled fashion; an ontology service 40 which manages a persistent representation of the ontologies used within the system and also manages export of ontology data in a format suitable for use by the information extraction engine as well as import of ontology data from the target database; and a pipeline manager service 42 which comprises a web tier providing a computer-user interface adapted to allow the initiation and monitoring of curation jobs and a service layer which encapsulates the core functionality for handling curation jobs. A database persistence layer 44 provides control logic to allow data to be persisted uniformly to the relational database management system 18 using the Hibernate object/relational persistence and query service or customised SQL via JDBC (JDBC is a trade mark of Sun Microsystems, Inc. Hibernate is an open source project described at www.hibernate.org). Information extraction is decoupled via a JMS queue 45 and managed by information extraction engine 46 which interfaces with natural language processing (NLP) pipeline 48. Another important part of the system is a target mapping control module 50 which maps output data from the target service to a target database.

Document Retrieval

Figure 4:
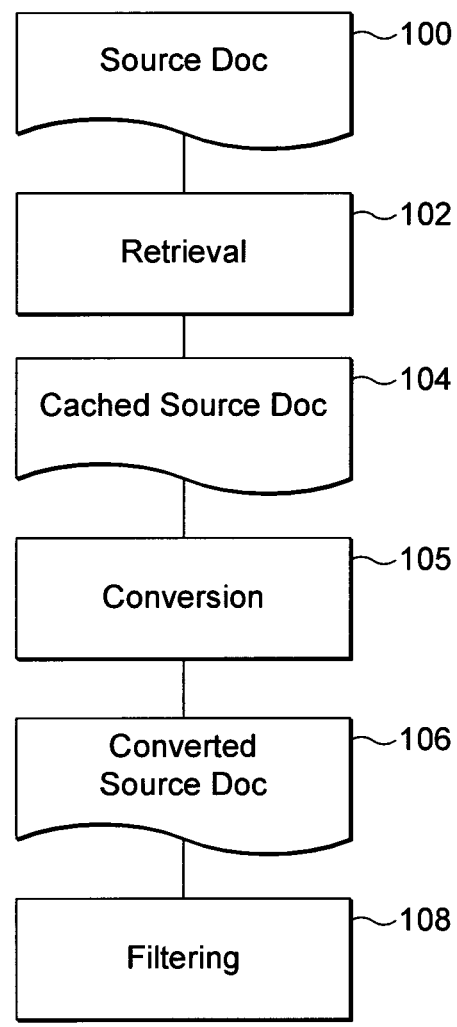
FIG. 4 is a flow diagram of the steps involved in retrieving documents files and filtering them prior to information extraction.

In use, document files are retrieved from external sources under the control of the pipeline manager service. FIG. 4 is a flow diagram of the steps involved in retrieving documents files and filtering them prior to information extraction. Document files 100 are retrieved 102 from one or more remote sources and cached 104. Document files may be received which fulfil a particular search query, or according to predetermined criteria. For example, documents fulfilling certain criteria may be automatically retrieved periodically from PubMed (www.ncbi.nlm.nih.gov/entrez/query.fcgi).

Document files are then converted 105 into a different format if need be. Document files are converted into XML files including plain text with no, or relatively little mark-up. A software module is provided for converting document files in portable document format (PDF) to XML. It is important that these document files are not XML marked-up files which have simply had the XML mark-up removed. This is because text obtained by removing mark-up from a marked up XML source will not always be the same as that obtained directly from an original plain text source. For example, an XML marked-up document might annotate a protein fragment using subscripts or superscripts to identify the particular fragment. For example, if the XML mark-up was removed from XML mark-up denoting text fragment $ABC^{12-37}$, the resulting plain text would be ABC12-37. However, the same document from an original plain text source may mark this up as ABC12-37 or ABC 12-37 or ABC(12-37) or ABC[12-37].

The converted document files are stored 106 and both the original retrieved document files and the converted document files are retained in storage. Document files (which have been converted if need be) are optionally filtered 108 to determine those of most relevance.

Information Extraction

Figure 5:
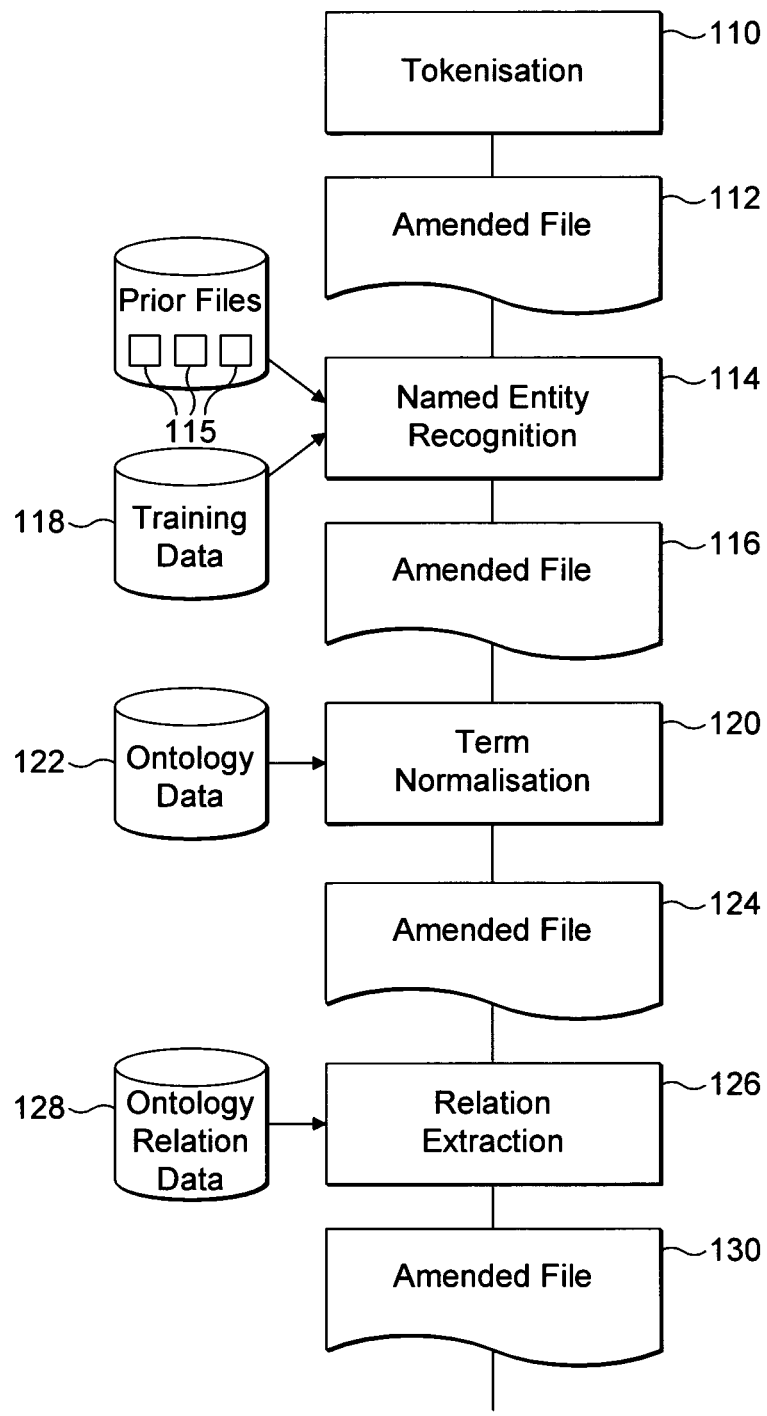
FIG. 5 is a flow diagram of the steps involved in information extraction.

FIG. 5 is a flow diagram of the steps involved in the subsequent information extraction procedure. A tokenisation software module 110 accepts a cached document file in XML format as input and outputs an amended XML file 112 including tokenisation mark-up. A named entity recognition software module 114 receives the amended XML file 112 as input and outputs a further amended XML file 116 in which individual instances of entities have been recognised and marked-up. The named entity recognition software module 114 has been previously trained on training data 118. The named entity recognition software module comprises a plurality of different prior files which function as data which determines the performance of the named entity recognition software module. Different prior files 115 which have been amended to provide different balances between precision and recall have been provided for use in extracting data for review by different curators. Training data 118 is described further below. The amended XML file 116 is then processed by a term normalisation software module 120 which also takes ontology data 122 as an input, outputting a further amended XML file 124 in which individual instances of entities have been labelled by reference to normalised forms of the entity stored in the ontology data. The amended XML file 124 is then processed by a relation extraction software module 126 which outputs an annotated XML file 128 including data concerning relations which have been identified in the document file.

Tokenisation, named entity recognition, term normalisation and relation extraction are each significant areas of ongoing research and software for carrying out each of these stages is well known to those skilled in the field of natural language processing. In an exemplary information extraction pipeline, input documents in a variety of formats, such as pdf and plain text, as well as XML formats such as the NCPI/NLM archiving and interchange DTD, are converted to a simple XML format which preserves some useful elements of a document structure and formatting information, such as information concerning superscripts and subscripts, which can be significant in the names of proteins and other biomedical entities. Documents are assumed to be divided into paragraphs, represented in XML by <p> elements. After tokenisation, using the default tokeniser from the LUCENE project (the Apache Software Foundation, Apache Lucene, 2005) and sentence boundary detection, the text in the paragraphs consists of <s> (sentence) elements containing <w> (word) elements. This format persists throughout the pipeline. Additional information and annotation data added during processing is generally recorded either by adding attributes to words (for example, part-of-speech tags) or by standoff mark-up. The standoff mark-up consists of elements pointing to other elements by means of ID and IDREF attributes. This allows overlapping parts of the text to be referred to, and standoff elements can refer to other standoff elements that are not necessarily contiguous in the original text. Named entities are represented by <ent> elements pointing to the start and end words of the entity. Relations are represented by a <relation> element with <argument> children pointing to the <ent> elements participating in the relation. The standoff mark-up is stored within the same file as the data, so that it can be easily passed through the pipeline as a unit, but one skilled in the art will recognise that the mark-up may be stored in other documents.

Input documents are then analysed in turn by a sequence of rule-based pre-processing steps implemented using the LT-TTT2 tools (Grover, C., Tobin, R. and Matthews, M., Tools to Address the Interdependence between Tokenisation and Standoff Annotation, in Proceedings of NLPXML2-2006 (Multi-dimensional Markup in Natural Language Processing), pages 19-26. Trento, Italy, 2006), with the output of each stage encoded in XML mark-up. An initial step of tokenisation and sentence-splitting is followed by part-of-speech tagging using the C&C part-of-speech tagger (Curran, J. R. and Clark, S., Investigating GIS and smoothing for maximum entropy taggers, in Proceedings of the 11th Meeting of the European Chapter of the Association for Computational Linguistics (EACL-03), pages 91-98, Budapest, Hungary, 2003), trained on the MedPost data (Smith, L., Rindflesch, T. and Wilbur, W. J., MedPost: a part-of-speech tagger for biomedical text. Bioinformatics, 20(14):2320-2321, 2004).

A lemmatiser module obtains information about the stems of inflected nouns and verbs using the Morpha lemmatiser (Minnen, G., Carroll, J. and Pearce, D., Robust, applied morphological generation, in Processing of 1st International Natural Language Generation Conference (NLG '2000), 2000). Information about abbreviations and their long forms (e.g. B cell linker protein (BLNK)) is computed in a step which calls Schwartz and Hearst's ExtractAbbrev program (Schwartz, A. S. and Hearst, M. A. Identifying abbreviation definitions in biomedical text, in Pacific Symposium on Biocomputing, pages 451-462, 2003). A lookup step uses ontology information to identify scientific and common English names of species for use downstream in the Term Identification component. A final step uses the LT-TTT2 rule-based chunker to mark up noun and verb groups and their heads (Grover, C. and Tobin, R., Rule-Based Chunking and Reusability, in Proceedings of the Fifth International Conference on Language Resources and Evaluation (LREC, 2006), Genoa, Italy, 2006.)

A named entity recognition module is used to recognise proteins, although one skilled in the art will recognise that other classes of entities such as protein complexes, fragments, mutants and fusions, genes, methods, drug treatments, cell-lines etc. may also be recognized by analogous methods. The named entity recognition module was a modified version of a Maximum Entropy Markov Model (MEMM) tagger developed by Curran and Clark (Curran, J. R. and Clark, S., Language independent NER using a maximum entropy tagger, in Walter Daelemans and Miles Osborne, editors, Proceedings of CoNLL-2003, pages 164-167, Edmonton Canada, 2003, hereafter referred to as the C&C tagger) for the CoNLL-2003 shared task (Tiong Kim Sang, E. F. and De Mulder, F., Introduction to the CoNLL-2003 shared task: Language-independent named entity recognition, in Walter Daelemans and Miles Osborne, editors, Proceedings of CoNLL-2003, pages 142-147, Edmonton, Canada, 2003).

The vanilla C&C tagger is optimised for performance on newswire named entity recognition tasks such as CoNLL-2003, and so a tagger which has been modified to improve its performance on the protein recognition task is used. Extra features specially designed for biomedical text are included, a gazetteer containing possible protein names is incorporated, an abbreviation retagger ensures consistency with abbreviations, and the parameters of the statistical model have been optimised. The addition features which have been added using the C&C experimental feature option are as follows: CHARACTER: A collection of regular expressions matching typical protein names; WORDSHAPE: An extended version of the C&C 'wordtype' orthographic feature; HEADWORD: The head word of the current noun phrase; ABBREVIATION: Matches any term which is identified as an abbreviation of a gazetteer term in this document; TITLE: Any term which is seen in a noun phrase in the document title; WORD-COUNTER: Matches any non-stop word which is among the ten most commonly occurring in the document; VERB: Verb lemma information added to each noun phrase token in the sentence; FONT: Text in italics and subscript contained in the original document format. NOLAST: The last (memory) feature of the C&C tagger was removed. The modified C&C tagger has also been extended using a gazetteer in the form of a list of proteins derived from RefSeq (http://www.ncbi.nlm-.nih.gov/RefSeq/), which was pre-processed to remove common English words and tokenised to match the tokenisation imposed by the pipeline. The gazetteer is used to tag the proteins in the document and then to add the bio tag corresponding to this tagging and the bigram of the previous and current such bio tags as C&C experimental features to each word. Cascading is carried out on groups of entities (e.g. one model for all entities, one for specific entity type, and combinations). Subsequent models in the cascade have access to the guesses of previous ones via a GUESS feature. The C&C tagger corresponds to that described in B. Alex, B. Haddow, and C. Grover, Recognising nested named entities in biomedical text, in Proceedings of BioNLP 2007, p. 65-72, Prague, 2007, the contents of which are incorporated herein by virtue of this reference.

In use, the C&C tagger employs a prior file which defines parameters which affect the function of the tagger. A plurality of different prior files are provided to enable named entity recognition to be carried out with different balances between precision and recall, thereby enabling information extraction to take place in a plurality of different operating modes in which different data is extracted for subsequent review by the human creator. The "tag prior" parameter in each prior file is selected in order to adjust the entity decision threshold in connection with each of the bio tags and thus modify the decision boundary either to favour precision over recall or recall over precision.

The abbreviation retagger is implemented as a post-processing step, in which the output of the C&C tagger was retagged to ensure that it was consistent with the abbreviations predicted by the Schwarz and Hearst abbreviation identifier. If the antecedent of an abbreviation is tagged as a protein, then all subsequent occurrences of the abbreviation in the same document are tagged as proteins by the retagger.

The term identification software module employs four key components. The first component is a species tagger which identifies the most likely species of individual mentions of entities in a document by looking at the context of each mention of an entity. The species tagger focuses particularly on clues from species-indicating words, such as "human" or "mouse". The species tagger makes use of a Weka implementation of the Support Vector Machines algorithm (www.cs.waikato.ac.nz/ml/weka, Witten, I. H. and Frank, E. (2005), Data Mining: Practical machine learning tools and techniques, second edition, Morgan Kaufmann, San Francisco, 2005), which has been trained on manually annotated data. In one implementation, each training instance is represented as a features-value pair, where features are TF-IDF weighted word lemmas that co-occur with the protein mentioned in a context window of size 50, and a value is the species which has been assigned to the protein mentioned by a human annotator. The species tagger may output not only the most likely identified species, but also a number of alternative species.

After species identification, both a fuzzy matcher and a rule-based matcher are invoked, each of which independently identifies surface forms which are similar to the mention of an entity, which are known synonyms of entities, within the ontology. The output from this stage is a series of suitcases, one of which is provided for each surface form. The suitcase concerning each surface form includes identifiers of entities from the ontology which have a synonym which is the same as the respective surface form.

A ranking module then reads the suitcases and produces a ranked list of candidate identifiers for each mention of an entity in the text document. The ranking module can employ a heuristic rule which favours identifiers which have the lowest numerical value in the ontology; which takes into account the number of references to the identifier in the RefSeq ontology; and which also takes into account whether an instance of an entity is identical or similar to the canonical form of the entity to which a candidate identifier relates, rather than a synonym of the entity; and, where relevant, the amino acid length of a protein to which a candidate identifier relates and/or the number of the isoform to which a candidate identifier relates (that is to say, the numerical index in entities which exist in isoforms, such as CK-1, CK-2 and CK-3). Applying standard experiments, familiar to one skilled in the art, results in determining a weighting for these various factors and an ordering for processing them that produces the best performance for any given set of training data.

The result is a bag of typically up to 15 candidate identifiers output in connection with each mention of an entity. The candidate identifiers in each bag are those which are considered to be the most likely identifiers of each individual mention of an entity and they are provided in a ranked order. Information concerning each of the candidate identifiers may be provided to a curator, enabling a curator to select a preferred identifier from the candidate identifiers. To increase the number of entries in the list which is provided to a curator, additional potentially relevant candidate identifiers may be obtained from the suitcase concerning the surface form which corresponds to each mention of an entity. Alternatively, a term identification software module which outputs a single most likely identifier may be employed.

After term identification, a relation extraction module uses simple contextual features to detect binary relations between proteins (Protein-Protein Interactions) in the digital representations of documents. For every pairing of proteins within a sentence, a relation candidate is created and its relevant features extracted. Probabilities are assigned to each instance using a Maximum Entropy Classifier (available from homepages.inf.ed.ac.uk/s0450736/maxent_toolkit.html), and those instances with probabilities which exceeded a threshold are accepted as relations. The features used are: the combination of the indices of the protein mentions of the interaction "P1-position:P2-position"; the combination of the lexical forms of the protein mentions of the interaction "P1:P2"; the lexical form, stemming/lemmatisation, part-of-speech tag and chunking information in a three-word context around the protein mentions; the distance, in tokens, between the two protein mentions; the number of other identified protein mentions between the two protein mentions; whether there is a coordination of negation structure between protein mentions; whether the document is an abstract or full paper; normalised forms of the protein mentions; concatenation of the words between proteins, and another features using the part-of-speech tags in the same manner; words between and right before/after proteins in a bag-of-words approach; bigrams and trigrams around protein mentions. The relation extraction module also uses the following information: a protein/gene interaction corpus derived from the BioCreAtIvE task 1A data, as additional training data (described in Plake, C., Hakenberg, J. and Leser, U., Optimizing syntax-patterns for discovering protein-protein-interactions, in Proc ACM Symposium on Applied Computing, SAC, Bioinformatics Track, volume 1, pages 195-201, Santa Fe, USA, March 2005); a list of "interaction words" which have been determined to be information of when a protein-protein interactions occurs, such as interact, bind, inhibit, phosphorylation, were used for some features; the twenty-two syntactic patterns used in Plake et al., are each used as boolean features in regular expression form: "P1 word {0,n} Iverb word {0,m} P2". All of the following features are extracted for the nearest interaction words found before, between and after each pair of protein mentions: whether an interaction word exists within a window of fifteen tokens; the distance between the interaction word and the protein it is closest to; the lexical form and part-of-speech tag of the interaction word; whether the interaction word is a Head Verb or Noun; and how many interactions words there are in the sentence.

Example Document

FIG. 6 is an example of a document suitable for processing by the system. FIG. 7 is an XML file of the same document included within the title and body tags of an XML file suitable for processing by the system. The body of the text is provided in plain text format within body tags. FIGS. 8A, 8B, 8C and 8D are successive portions of an annotated XML file concerning the example document after information extraction by the procedure described above.

The annotated XML file includes tags concerning instances of entities 200 (constituting annotation entity data). Each tag specifies a reference number for the instance of an entity (e.g. ent id="e4"), the type of the entity (e.g. type="protein"), the confidence of the term normalisation as a percentage (e.g. conf="100") and a reference to ontology data concerning that entity, in the form of a URI (e.g. norm=http://www.cognia.com/txm/biomedical/#protein_P00502885). (The reference to ontology data concerning that entity constitutes an identifier of an instance of an entity which is a reference to ontology data). Tags concerning each instance of an entity are included inline within the XML file just before the word (with a <w> prefix and </w> suffix) to which the data relates (thereby constituting data which specifies the location of the identified instance of the entity within the digital representation of the document).

The annotated XML file also includes a document identifier 202, as well as data specifying the source of the document which the document file represents 204 and information concerning the parameters of the search carried out to retrieve the original document file 206.

Relations which have been identified in the text are recorded as standoff annotation at the end of the annotated XML file (FIGS. 8C and 8D). Annotation data concerning an instance of a relation 220 (constituting annotation relation data) includes a reference number 222 for that instance of a relation, the confidence 224 of the relation extraction as a percentage, normalised form of the entities which the relation concerns 226, the type of the entity 228 (e.g. type="ppi" denotes a protein-protein interaction), and the reference numbers 230, 232 of the entities which the relation concerns.

FIG. 9 is the document of FIG. 6 with the entities annotated in the XML file of FIGS. 8A to 8D underlined and the relations annotated in the XML file of FIGS. 8A to 8D indicated. Note that although the information extraction procedure has produced generally reliable results, there are errors. In particular, relation R6 is wrong and a further relation 250 has not been identified.

Following information extraction, the annotated XML file is stored in the relational database management system. At a later stage, the annotated XML file is curated via a curation tool computer-user interface, allowing a human curator to add, delete and amend annotation data. For example, in the case of the annotated document shown in FIG. 9, a human curator may delete or correct relation R6 and manually add further relation 250. As well as allowing a human curator to add, delete and amend curation data, the curation tool computer-user interface also allows the human curator to select data for output to a target database.

Curation

The curation tool computer-user interface is implemented by the web service component delivering a Java application to a computer which executes the application, as well as the annotated XML file relating to the document to be curated. A user interacts with the interface via the computer's monitor and input peripherals such as a keyboard and computer mouse.

Figure 10:
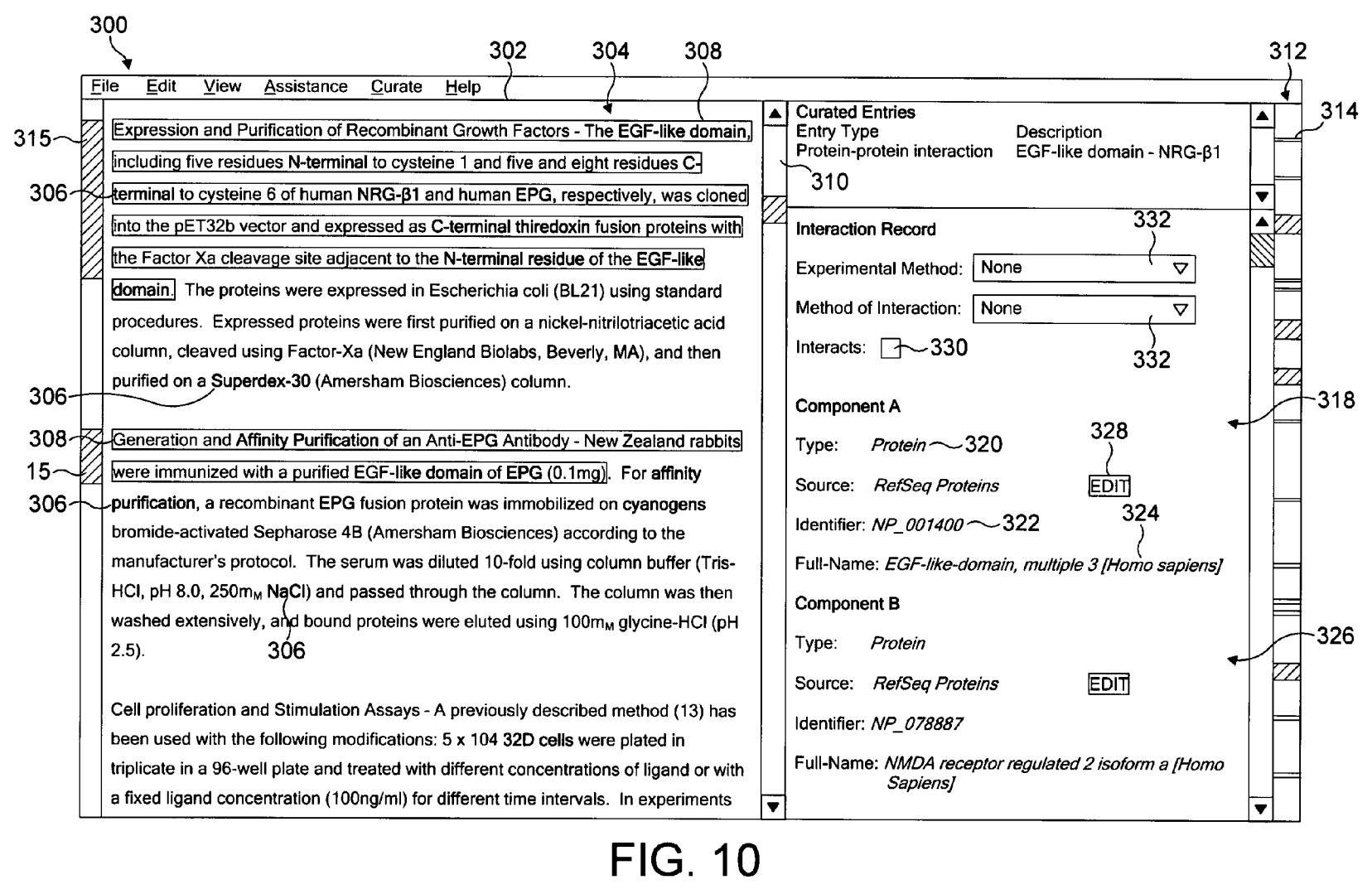

FIG. 10 is a screenshot of a curation computer-user interface 300. The computer-user interface displays a document display window 302 (functioning as the first region) showing a document 304. Individual instances of entities 306 are highlighted at the location in the document which is specified by the annotation data (i.e. by the location of the tag concerning that instance of an entity within the XML file). In this example, each instance of an entity is highlighted by rendering it in bold. Not all instances of entities have been labelled, for clarity. Entities may be highlighted only in response to a request by a user (e.g. by selecting a menu option), or may be highlighted at all times. Accordingly, a part of the document which is visible within the document display window includes annotations (bold text) to highlight entities which were identified by the natural language processing pipeline. Within the document display window, relations 308 are annotated by highlighting them with a box around the text which describes the relation. The box may, for example, be in colour. The document display window further comprises a standard window scroll bar 310 enabling a user to scroll through the document.

The curation computer-user interface further includes a navigation tool in the form of a first elongate bar 312 which indicates features of the document which have been automatically identified by representing them with a colour bar 314 or other visual indicator at a position in the elongate bar which is proportional to their location within the document. Different types of features, such as protein mentions or other named entities, identified relations, or automatically identified section headings (such as "Introduction", "Materials and Methods" etc.) are displayed using different coloured bars or visual indicators. A second elongate bar 314 is an expanded representation of the features indicated in the first elongate bar which are visible in the section of the document which is currently displayed in the document display window. For example, a coloured bar 315 is provided alongside each identified relation. The second elongate bar is dynamically updated when the section of the document which is displayed is changed using the scrolls bar or other computer-user interface feature. The annotations representing entities and relations at their identified location within the document facilitate easy identification of relevant sections of the document, which require detailed study, by the curator.

The user-interface also provides means for a user to select a relation which has been automatically identified using a pointing device, such as a mouse, or another computer-user interface feature responsive to which provisional amended annotation data is prepared from the automatically identified annotation data concerning the selected relation. The provisional amended annotation data is then represented in an annotation amendment window 316. The annotation amendment window comprises a first section 318 which represents data concerning the entity which is the first component of a relation, including details of the type of entity 320 (e.g. protein), and the identifier 322 of the entity which was automatically identified during the natural language information extraction procedure. A canonical form of the name of the entity 324, obtained from the ontology, is also displayed. Corresponding information is provided in a second section 326 of the annotation amendment window in connection with the second entity which the relation concerns.

A curator may accept the provisional amended annotation data as correctly representing the relation and indicate using a user-interface feature (such as a button or menu choice) that the provisional amended annotation data is correct and should be used to create output data for export to a target database. However, the curator may also amend the provisional amended annotation data, for example they may select a user-interface feature such as a button 328 which enables them to edit the data concerning one or both of the identified entities using common user-interface features such as check boxes 330, text boxes, drop-down menus 332, lists etc. Thus, the curator may correct erroneous annotation data, for example an incorrect identification of an entity, or add annotation data which was omitted by the information extraction procedure (for example, an omitted entity). Added annotation data may include data which the information extraction procedure is not capable of extracting. For example, where the information extraction procedure is capable of identifying an entity, but not capable of identifying a property of the entity, this data can be input by a user, thereby obtaining an efficiency benefit from the user of an information extraction procedure, without the disadvantage of being able only to output data derived from the information extraction procedure. A curator may also create an entirely new provisional amended annotation data record. For example, they may create provisional amended annotation data concerning a relation which was not identified by the information extraction procedure, and then edit the provisional amended annotation data.

Examples of annotation data concerning entities which may be viewed and/or edited include the type of entity, the identifier of the entity, the canonical form of the entity, properties of the entity (e.g. whether and how it is modified). Examples of relation data concerning relations which may be viewed and/or edited include the identifiers of the entities which the relation concerns, a description of the relation and properties of the relation, e.g. the experimental method which lead to the relation (e.g. affinity purification), the method of interaction (e.g. phosphorylation) and whether the relation concerns an interaction.

Once the provisional annotation data concerning an entity (provisional annotation entity data) or a relation (provisional annotation relation data) has been edited, the resulting data is considered to be curated (i.e. approved by a curator) and stored for export to a target database, in whole or in part, as output data. Essentially, one or more records which constitute provisional annotation data have been pre-populated using annotation data which was prepared by the information extraction procedure, and then edited before being selected for export to a target database.

An example of the annotation relation data which could be stored for export is as follows:
"Between character offset 100 and character offset 200 of Document ID 123 which is from the "Medline Abstract" collection and has PubMed ID 456, 'p19' (protein p19, ontology ID 135) and 'ADP ribosylation factor' (protein Arf, ontology ID 680) are said to interact."

Thus, the annotation relation data may include a reference to the start and end locations of a fragment of text which refers to a particular relation ('character offset 100' and 'character offset 200'), as well as document identifiers (including internal document identifier, 'Document ID 123', and corresponding external document identifier, 'PubMed ID 456') and an identifier of the source ("Medline Abstract" collection) of the documents, as well as both the text denoting the related entities both as it is found in the document ('p19', 'ADP ribosylation factor) and in its normalised form ('p19' and 'Arf'). The annotation relation data can also include the type of the entities ('protein') and their IDs within ontology data ('ontology ID 680' and 'ontology ID 135') as well as details of the nature of the relation ('are said to interact').

One skilled in the art will recognise that the above annotation relation data could be stored in many different ways. Some or all of the annotation relation data may be exported to the target database.

In the above example, the annotation data in the input XML file is not amended. In an alternative embodiment, rather than editing provisional annotation data to form amended annotation data which is separate to the XML file concerning the edited document, the annotation data in the XML file, which was originally generated by the information extraction procedure, is amended. For example, where the document is received in the form of an XML file including annotation data, the curating procedure may finish by outputting an XML file including amended annotation data. In some circumstances, this would not be desirable because additional processing would be required to edit an XML file to reflected changes in annotation data in comparison to simply outputting curated provisional annotation data without the additional computing step of amending the annotation data included in an XML file. However, it may be advantageous to amend the underlying annotation data in certain circumstances, particularly when using the system to prepare training data for use in training a machine learning-based information extraction module.

Optionally, a local copy in system memory of annotation data in or relating to the input XML file may be amended during the editing procedure and used to dynamically update the display of the document with annotations.

Figure 11:
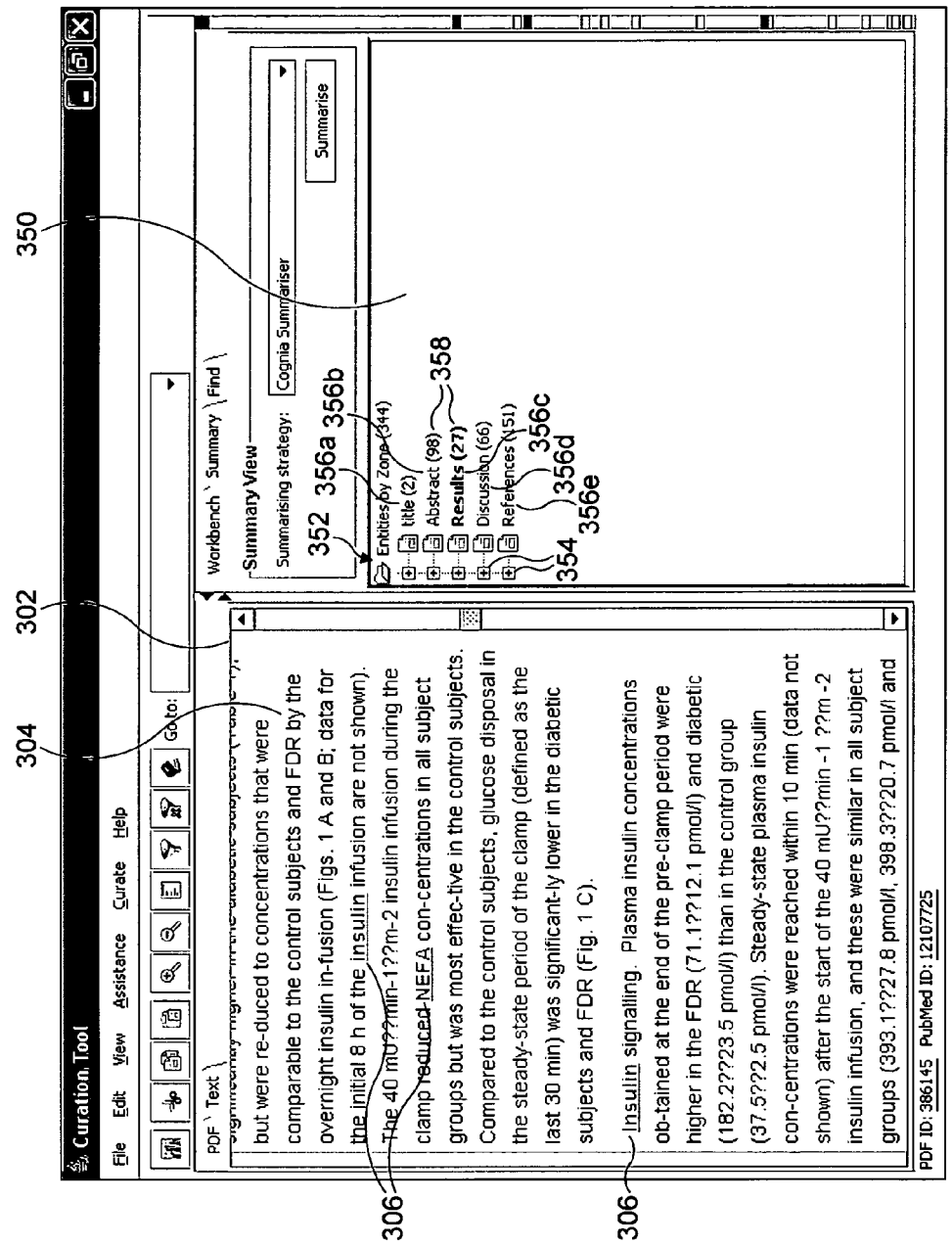
FIG. 11 is a screen shot of a curation computer-user interface.
Figure 12:
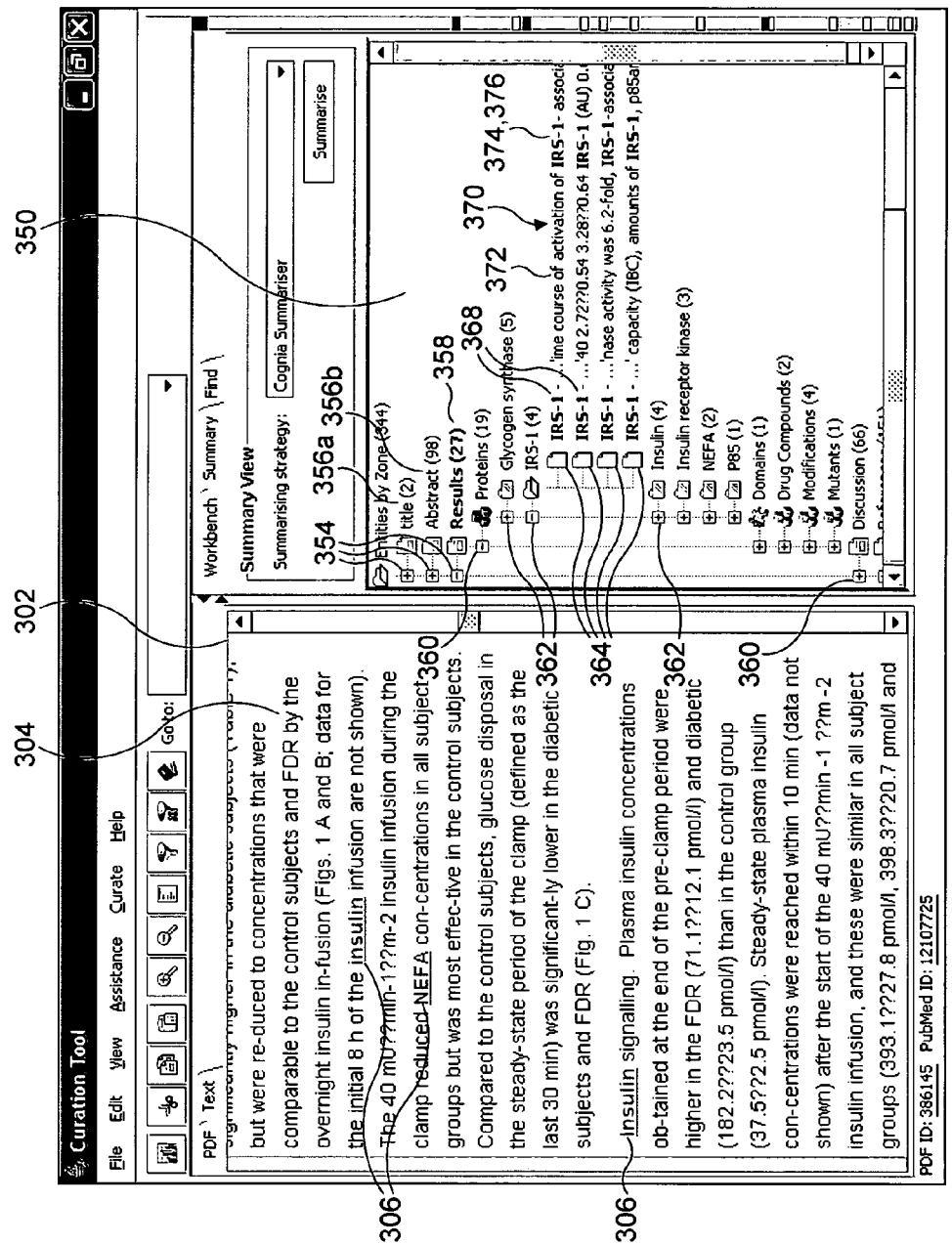
FIG. 12 is a screen shot of the curation computer-user interface of FIG. 11 after expansion of a tree diagram.

With reference to FIGS. 11 and 12, the curation tool computer-user interface has a user selectable summary mode in which it simultaneously displays a document display window 302 (functioning as the first region of the display) showing a user selectable portion of the digital representation of the document 304 with entities and/or relations highlighted at their identified location in the document, as well as a navigation window 350 (functioning as the second region of the display). In the user selectable summary mode, the curation tool computer-user interface provides information about instances of entities which have been automatically identified by the NLP pipeline. Accordingly, the user selectable summary mode enables a curator to rapidly find, and view the context of, automatically identified instances of entities.

The user may selectably view different portions of the digital representation of the document in the document display window, and thereby select which portion is visible, using conventional user interface elements, such as scroll bars, and input devices, such as a keyboard or mouse.

The navigation window presents information about entities and/or relations which have been identified within the digital representation of a document in the form of a branching tree 352 with user selectable node elements 354. Node elements are logically arranged in a branching tree with each node element having either or both a parent node element or one or more child elements and a user selectable portion of the tree is visible at any given time. Some of the node elements are leaf node elements which relate to individual instances of entities which have been automatically identified in the digital representation of a document and the navigation window provides a user interface enabling a user to rapidly view data concerning individual instances of entities which have specific values of one or more properties (such as location in the document, type etc.).

Node elements other than leaf node elements (referred to herein as non-leaf node elements) are user selectable and, when selected, toggle whether or not the child node elements of the user selected node element are displayed. As can be seen from FIGS. 11 to 13, the arrangement in which the node elements are displayed visually represents the tree structure, with child nodes located adjacent to their parent node, for example in the form of a list underneath and optionally to one side of the parent node.

The tree diagram has different user selectable node elements concerning different zones of the digital representation of a document, namely the title 356a, abstract 356b, results section 356c, discussion section 356d and reference section 356e. Each of these node elements is therefore associated with a section of the document and each node element associated with a section of the document has, as its ultimate children, leaf node elements concerning identified instances of entities which have the property of having been automatically identified as being in that section of the document. In the highest level view, shown in FIG. 11, the name of each zone is displayed along with a number 358 indicating the number of automatically identified entities in each zone. The grouping by zone within the document is helpful in that it enables a curator to view the distribution of instances of entities within a document and/or to navigate rapidly to instances of entities in the zone which they wish to review.

Once the tree diagram has been opened up by selecting a first level node element, a separate second level node 360 element is listed, adjacent to the selected first level node element, in relation to each type of entity which has been identified in the appropriate section of the digital representation of the document, for example, proteins, domains, drug compounds, modifications and mutants. Accordingly, each second level node is therefore associated with the type of an entity and each has, as its ultimate children, leaf node elements concerning identified instances of entities which are of the respective entity type.

A user may select a second level node, whereupon the tree diagram opens up to show third level nodes 362 provided in respect of each entity of the respective type of which at least one instance has been identified in the respective section of the document. Finally, fourth level nodes 364, each of which is a leaf node element relating to an individual instance 366 of an entity which has been identified in the document are displayed responsive to a user selecting a third level node.

The fourth level nodes are formed into a list of individual instances of a selected entity within the relevant section of the digital representation of a document. Each instance is represented by a canonical form of the entity 368 and a text snippet 370 in the form of a segment of text 372, from the digital representation of a document, which extends to either side of the individual instance of the selected entity. The actual mention 374 of the individual instance within the segment of text is highlighted 376. The entire line of text relating to an individual mention of an entity (including the canonical form of the entity), or the segment of text, or the actual mention of the instance of an entity, functions as a user selectable user interface element.

Figure 13:
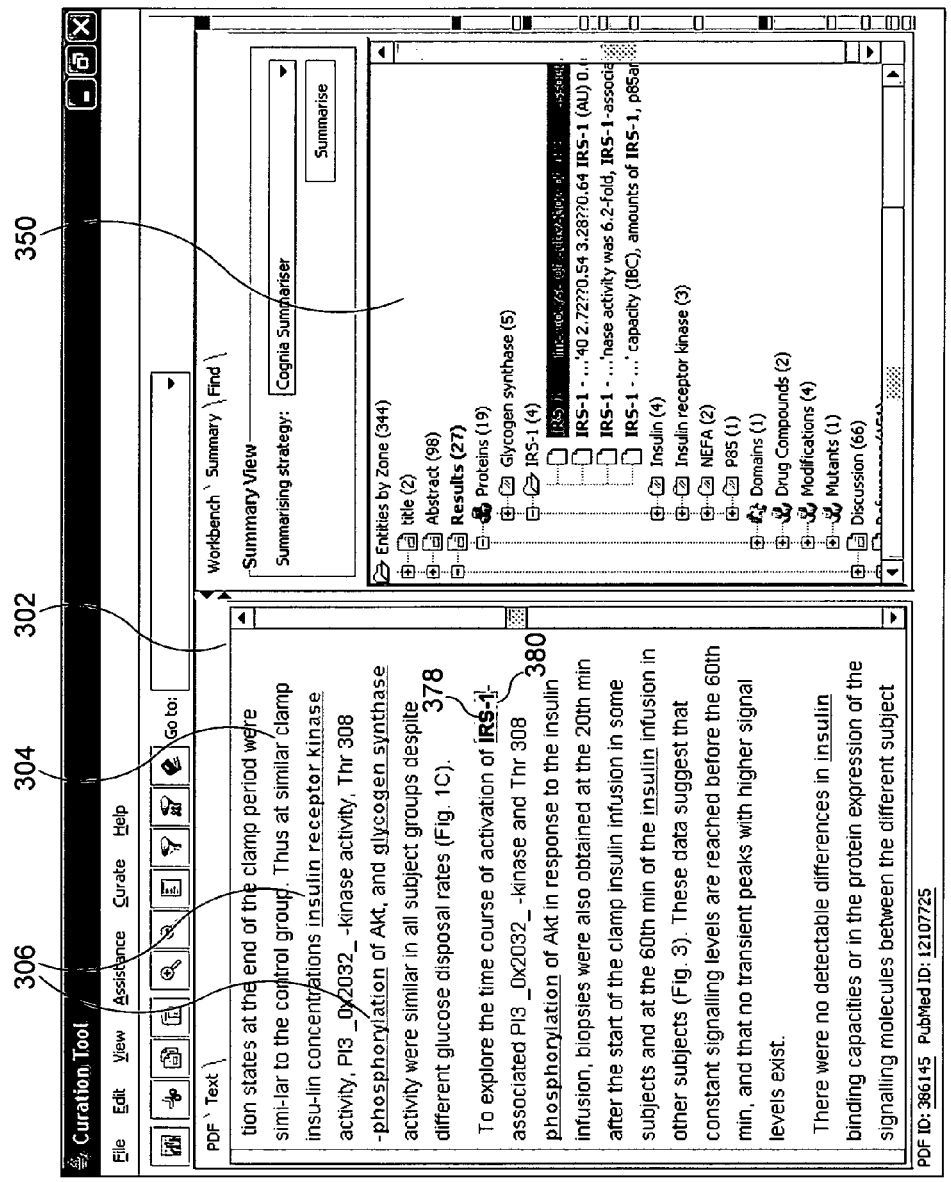
FIG. 13 is a screen shot of the curation computer-user interface of FIG. 12 after selection by a user of a user interface element.

A user may click on the user selectable user interface element using a pointing device such as a computer mouse. Responsive to selection of a user interface element, the display of the digital representation of a document in the document display window 302 is adjusted, as illustrated in FIG. 13, so that the portion of the digital representation of a document which is visible in the document display window is the portion which extends to either side of the selected individual instance of an entity, with the selected individual instance of an entity 378 approximately halfway up the displayed portion of a digital representation of a document. Although each identified instance of an entity is highlighted, the selected instance of an entity has additional highlighting 380 to draw a user's attention to the instance of an entity.

Accordingly, the tree structure branches such that, for each non-leaf node element, each child node element relates to a different value of the same property of the instances of entities associated with the leaf nodes which are the ultimate children of the respective child node element. For a non-leaf node element which is the parent only of leaf elements, each leaf element relates to an individual instance of an entity having the properties associated with the non-leaf node element, and non-leaf node elements above the non-leaf node element in the tree. In order to facilitate the display of different user selected node elements from the group of node elements in the tree structure, a user may click again on a non-leaf node element, whereupon the child node elements of the non-leaf node element disappear.

In this example, at each depth within the tree structure, for each node element which has non-leaf child node elements, child node elements are provided which are associated with different values of the same property. For example, different groups of second level node elements which are associated with the type of instances of entities are provided as child node elements for each first level node element. However, this need not be the case and child node elements could be provided which are associated with alternative values of different properties in respect of different non-leaf node elements at the same depth within the tree structure.

Typically, the properties which form the basis for the branching of the tree structure are determined by configuration parameters which are editable and/or selectable from groups of alternative configuration parameters, depending on the domain of knowledge which the digital representation of a document concerns.

Figure 14:
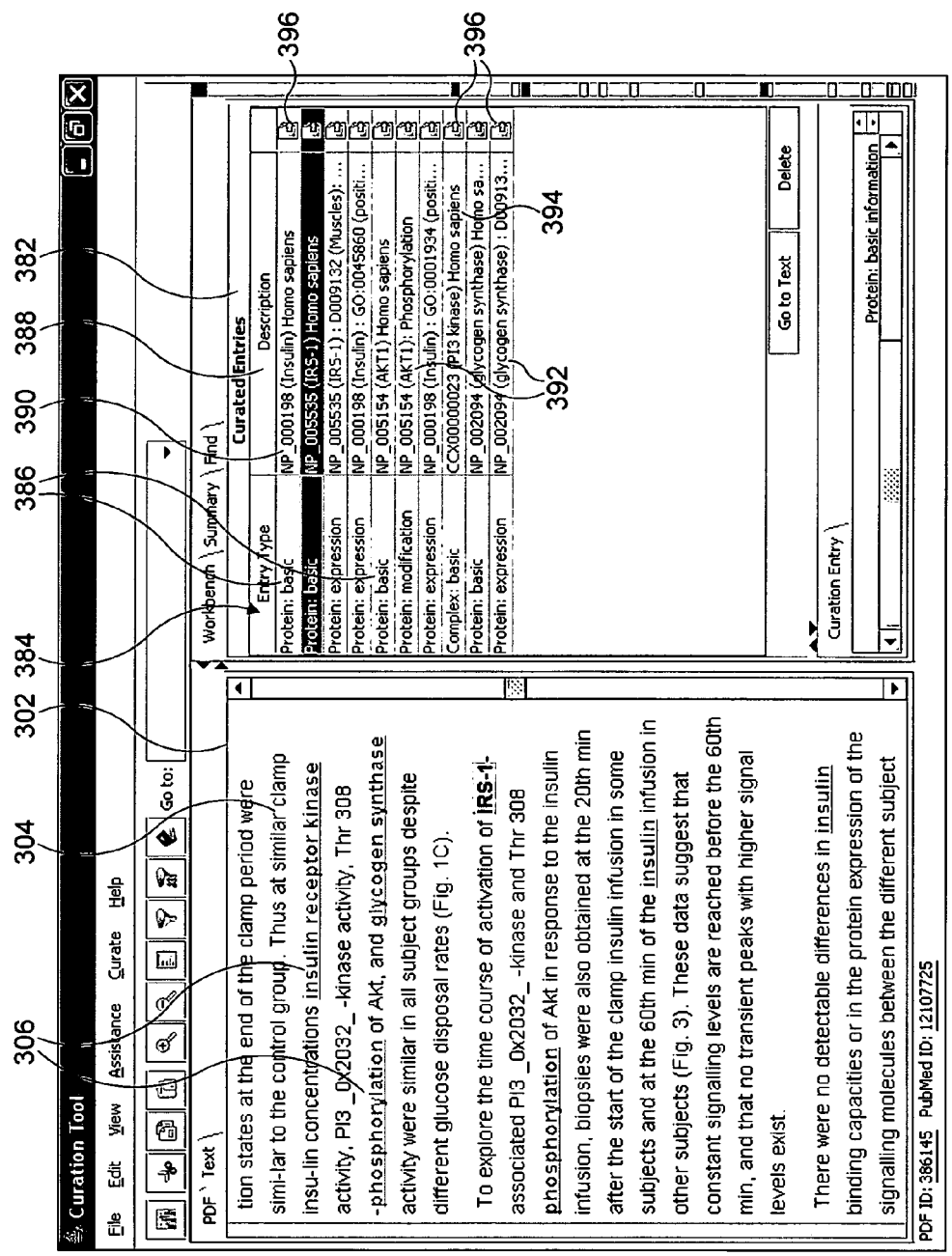
FIG. 14 is a screen shot of the curation computer-user interface of FIG. 13 in a different display mode.

FIG. 14 illustrates another user selectable operating mode of the curation tool computer-user interface, in which the document display window is as before. However, in this operating mode, a curated entity window 382 is displayed simultaneously to the document display window. A list of curated instances of entities 384 is displayed in the curated entity window. Each entry in the list concerns a respective curated instance of an entity. By a curated instance of an entity, we refer to an instance of an entity which was originally identified automatically or by a curator, for which the associated annotation entity data has been reviewed and/or input by a curator, amended if required, and selected for output to a database. The data shown in the list of curated instances of entities in this user selectable operating mode is typically taken from records which have been selected for output to the target database.

Each entry in the list includes a summary of the entity type 386 and a description 388 of curated annotation entity data ascribed to the instance of an entity, including an identifier of the entity 390 in a database of entity identifiers (here a RefSeq accession number), a canonical form of the entity 392 and the species of the entity 394. Each entry in the list also includes an icon 396 which functions as a user selectable user interface element which, when selected by a user, causes the display of the digital representation of a document in the document display window to be adjusted as before, so that the portion of the digital representation of a document which is visible in the document display window is the portion which extends to either side of the individual instance of an entity which the relevant list entry concerns, with the respective individual instance of an entity approximately halfway up the displayed portion of a digital representation of a document. Although each identified instance of an entity is highlighted, the instance of an entity which the relevant list entry concerns has additional highlighting to draw a user's attention to the instance of an entity, as before.

In order to review data for export to the target database, a curator must read the context around an individual mention of an entity (and/or relation) within the digital representation of a document. The user interface provided by the methods of the invention enables a curator to more rapidly find the section of a digital representation of a document which they must study in order to review and, if necessary amend and/or input, annotation data concerning individual instances of entities when curating a digital representation of a document. The curator, or a second curator checking the work of a first curator, can also check data concerning individual instances of entities in the operating mode illustrated in FIG. 14.

Export

Periodically, the target service exports curated data to the target database. The target service proceeds systematically through the data to be exported in turn, checking whether the data is already found within the target database. If it is not, then the data is inserted into the target database by calling the API of the target database or generating an SQL insert/update. It may be necessary to translate the data into an appropriate format for the target database. If the target database has different ontology data, it is necessary to translate these references. The procedure can be repeated or carried out concurrently to populate more than one target database.

A potentially important optional feature of the invention is the provision of feedback in which data produced by the curation process is used in the automatic analysis of future document files.

Feedback—Ontology Data

Figure 15:
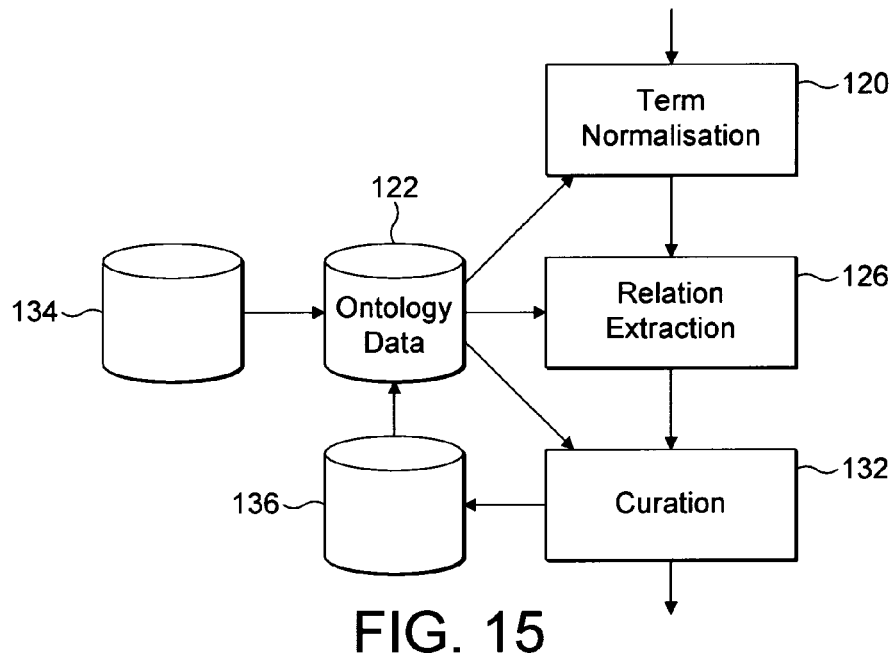
FIG. 15 is a schematic diagram of an ontology data feedback loop.

FIG. 15 is a schematic diagram of the feedback of ontology data for use in information extraction. Ontology data 122 concerning entities is used during the step of term normalization and ontology data concerning relations may also be used during the step of relation extraction. The ontology data used during these steps is a combination of predetermined ontology data 134 and new ontology data 136 added by curators during the curation process. This feedback procedure improves the reliability of the information extraction procedure, improving the cost-effectiveness and in some circumstances accuracy of the system as a whole. New ontology data can be added batchwise to the ontology data used for information extraction from time to time, or may be added immediately to the ontology data used for information extraction.

Figure 16:
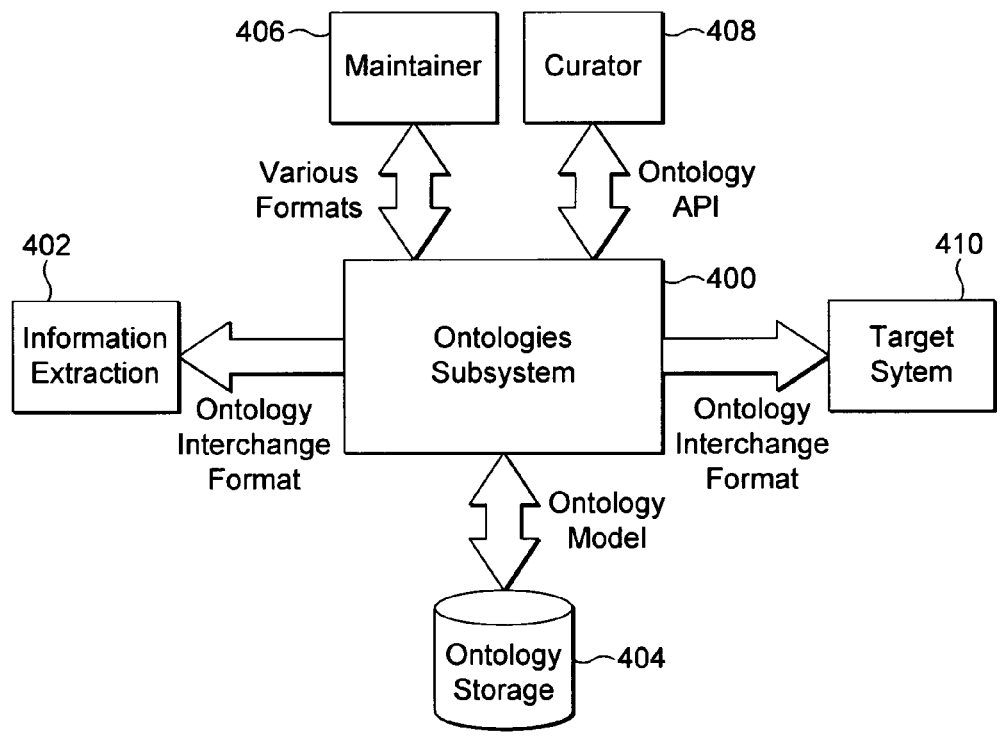
FIG. 16 is a schematic diagram of an ontology data maintenance system.

A more sophisticated ontology maintenance system is illustrated in FIG. 16. Ontology subsystem 400 provides ontology data concerning entities, and optionally relations, to information extraction module 402 (comprising tokenisation, named entity recognition, term normalisation and relation extraction modules). Ontology data is stored in ontology storage system 404 and the information extraction module is adapted to allow the ontology data to be amended by a maintainer 406 and by one or more curators 408. Furthermore, the information extraction module receives ontology data from target database 410, translating the format of the ontology data if required. This allows the ontology data to be updated as the target database is updated. A look-up table may be stored to allow references to entities (and optionally relations) in the information extraction and curation system to be mapped to entities (and optionally relations) in the target database.

In one example embodiment, the ontology data simply comprises a lexicon of entity names (for example, protein names). Each entity within the lexicon has a unique ontology identifier, a string denoting its normalised form, and strings denoting synonyms of the entity. A lexicon of this type can readily be prepared by extracting the relevant information from a more complex ontology.

Feedback—Training Data

Figure 17:
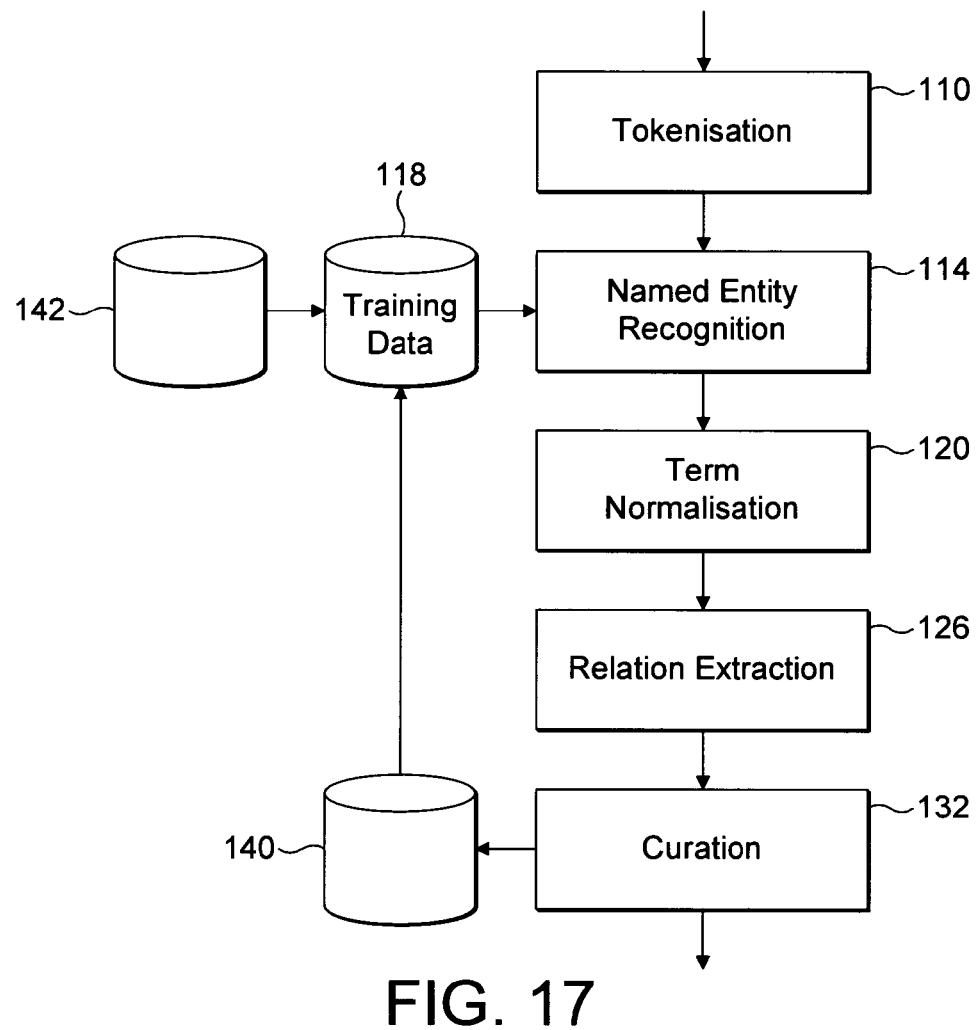
FIG. 17 is a schematic diagram of the feedback of training data within the system.

FIG. 17 is a schematic diagram of the feedback of training data within the system. The named entity recognition module is initially trained using training data which has been provided for the purpose and which typically consists of annotated document files which have been carefully checked to ensure that they are correctly annotated.

Whilst carrying out the curation process, the curator can select a document which they have been curating, or a part thereof, whereupon the annotated document file (or part thereof) resulting from their curation is stored in a database 140 of selected annotated document files. Periodically, the named entity recognition software module is retrained using training data 118 comprising both data from the database of selected annotated document files and also a database of predetermined annotated document files 142. In this case, the curation tool will typically enable a user to amend annotation data and to include the amended annotation data in an output XML file rather than to simply output data derived from the annotation data without amending the underlying annotation data included in the XML file.

One skilled in the art will recognise that other modules within the information extraction system could be retrained using training data selected in this way. An important benefit of selecting training data in this way is that the curators will be able to recognise when automatic analysis of a particular document file has been carried out badly by the information extraction system and so select document files of particular relevance for use in retraining.

Customisation

In use, the information extraction procedure functions according to one of a plurality of operating modes by carrying out named entity recognition using a selected prior file from amongst the prior files which are available. The named entity recognition software and a particular prior file together function as an information extraction module selected from a group of selectable alternative information extraction modules.

The prior files used by the named entity recognition module have been individually selected to display different balances between precision and recall by manually modifying the prior belief of the named entity tagger as to the likelihood of a token comprising the beginning of an entity, a subsequent part of an entity, or not being a part of an entity. This enables different curators within a group of curators to review different sets of data, for example some curators may review data extracted using an information extraction procedure which favours precision and other curators may review data extracted using an information extraction procedure which favours recall over precision. Alternatively, or as well, a group of curators may all review data which has been extracted using an information extraction procedure which favours precision over recall, or an information extraction procedure which favours recall over precision. However, different curators within the group may review data which favours precision over recall, or recall over precision respectively, to different extents. Thus, data may be extracted from many digital representations of documents using at least two information extraction operating modes, typically having different balances between precision and recall, and individual members of a team of human curators may review data extracted in different information extraction operating modes.

Information extraction can be carried out in the appropriate operating mode for a particular curator who will be reviewing the extracted data, or for a group of curators who are known to prefer a particular operating mode. In some embodiments, information extraction is carried out on the same document in two or more operating modes and a choice is subsequently made as to which set of extracted data is to be presented to a particular curator.

Although in this example, only the named entity recognition module has different operating modes with different balances between precision and recall, any stage of the information extraction pipeline, or combination of stages of the information extraction pipeline, can be optimised to a different balance between precision and recall. Conceivably, some of the stages of the information extraction procedure could be optimised to favour precision over recall and some of the stage of the information extraction procedure could be optimised to favour recall over precision.

Feedback

A suitable metric which is representative of the performance of a curator can be monitored in order to optimise the information extraction pipeline, either for that particular curator or in general. This can be used to try out alternative modules which implement individual stages of the information extraction pipeline or to optimise modules which implement individual stages of the information extraction pipeline.

Examples of suitable metrics include the time taken by a curator to review specified data, the rate of curation by a curator, the rate of error made by a curator relative to a gold standard, the number of mouse clicks or key presses made by a curator which reviewing specified data or the number of uses made by a curator of a search engine which is operable by the curator to retrieve data they might need while introducing or amending omitted or incorrectly extracted data during curation.

For example, a suitable metric may be a measurement related to the number of times that a curator uses a search engine. A curator may use a search engine when the automatic information extraction apparatus has not identifier, or has misidentified, an instance of a mention of an entity in a digital representation of a document. The search engine may be operable search in the RefSeq or MeSH lexicons.

These metrics can also be used to determine which information extraction operating mode leads to the best performance by an individual curator.

Consistency

The information extraction pipeline extracts data concerning individual mentions of entities, and allocates them an identifier, from the context of each individual mention of an entity. This has the effect that different instances of entities denoted by a particular character string may be allocated different identifiers at different locations in a digital representation of a document. Sometimes this will be correct, but this is not always the case.

In an alternative embodiment, the named entity recognition module is modified to force all chunks comprising having the same character string to be allocated the same entity type (e.g. protein, gene). One method of forcing all chunks with the same character string to be allocated the same entity type is, for each character string which is identified as representing an entity of a particular type, to propagate the same type to each chunk in the document having the same character string. Digital representations of documents are typically analysed from beginning to end and so the identifier allocated to the first instance of a character string will thereby be allocated to all subsequent instances of the same character string. A second method of forcing all named entities with the same character string to be allocated the same identifier is to carry out named entity recognition on the digital representation of the document and, for every character string which is recognized as a named entity on more than one occasion, to allocate each instance of that character string the identifier of the most frequently allocated identifier of that character string in the initial named entity recognition step. Different methods of forcing consistent interpretation of identical character strings may be implemented in different information extraction operating modes.

Documents which are cited above are incorporated herein by virtue of this reference.

Further modifications and variations may be made within the scope of the invention herein disclosed.

The invention claimed is:

1. A computer-implemented method of presenting data which has been automatically extracted from a digital representation of a document to a curator for review, the extracted data comprising annotation entity data concerning one or more instances of entities which have been identified in the digital representation of a document, the annotation entity data comprising data specifying the location of the identified instances of entities within the digital representation of a document, the method comprising the steps of:
   (i) displaying in a first region of a display screen a user selectable portion of the digital representation of a document with said instances of entities which are specified by the annotation entity data as being located within the displayed portion of the digital representation of a document highlighted at the location specified by the annotation entity data;
   (ii) displaying in a second region of the display screen a list of a plurality of instances of entities which have been identified in the digital representation of a document, at least one of the listed instances of an entity having a user selectable user interface element associated therewith;
   (iii) responsive to a user selecting the user selectable user interface element associated with an instance of an entity, adjusting the portion of the digital representation of a document which is displayed in the first region to include the location within the digital representation of a document where the instance of an entity associated with the selected user interface element is located;
   (iv) highlighting instances of relations identified as being located within the portion of the digital representation of a document which is displayed in the first region at the identified location of the identified instances of relations;
   (v) displaying in the second region of the display screen a list of a plurality of instances of relations which have been identified in the digital representation of a document, at least one of the listed instances of an relation having a user selectable user interface element associated therewith; and
   (vi) responsive to a user selecting the user selectable user interface element associated with an instance of a relation, adjusting the portion of the digital representation of a document which is displayed in the first region to include the location within the digital representation of a document where the instance of a relation associated with the selected user interface element is located.

2. A computer-implemented method according to claim 1, wherein the list of a plurality of instances of entities which have been identified in the digital representation of a document comprises or consists of automatically identified instances of entities.

3. A computer-implemented method according to claim 1, wherein the list of a plurality of instances of entities which have been identified in the digital representation of a document comprises or consists of identified instances of entities which have been reviewed by a curator.

4. A computer-implemented method according to claim 1, wherein the list of a plurality of instances of entities which have been identified in the digital representation of a document may comprise instances of entities which were not specified in the extracted data but were identified by a curator.

5. A computer-implemented method according to claim 1, comprising displaying a segment of text from the digital representation of a document, from around an individual instance of an entity, in the list of a plurality of instances of entities.

6. A computer-implemented method according to claim 5, wherein the user selectable user interface element comprises the segment of text concerning an individual instance of an entity, or a portion of the segment of text concerning an individual instance of an entity.

7. A computer-implemented method according to claim 1, wherein the step of adjusting the portion of the digital representation of a document which is displayed in the first region to include the location within the digital representation of a document where the instance of an entity associated with the selected user interface element is located comprises adjusting the portion of the digital representation of a document which is displayed in the first region so that the instance of an entity associated with the selected user interface element is located within a specific portion of the first region.

8. A computer-implemented method according to claim 1, wherein the list of a plurality of instances of relations is displayed at a different time to the list of a plurality of instances of entities.

9. A computer-implemented method according to claim 1, wherein the method further comprises providing a user with computer-user interface means for reviewing extracted data concerning instances of entities.

10. A computer-implemented method according to claim 9, wherein the method further comprises providing a user with computer-user interface means operable to receive new or amended data concerning instances of entities from a curator.

11. A computer-implemented method according to claim 9, wherein the method further comprises providing a user with computer-user interface means operable to receive data concerning instances of entities which have been identified within the digital representation of a document by a curator, but are not specified by the extracted data.

12. A computer-implemented method according to claim 1, comprising the step of automatically extracting annotation entity data concerning instances of entities using information extraction apparatus, to prepare the extracted data for review.

13. Computing apparatus operable to carry out steps of presenting data which has been automatically extracted from a digital representation of a document to a curator for review, the extracted data comprising annotation entity data concerning one or more instances of entities which have been identified in the digital representation of a document the annotation entity data comprising data specifying the location of the identified instances of entities within the digital representation of a document, the steps comprising;

(i) displaying in a first region of a display screen a user selectable portion of the digital representation of a document with said instances of entities which are specified by the annotation entity data as being located within the displayed portion of the digital representation of a document highlighted at the location specified by the annotation entity data;

(ii) displaying in a second region of the display screen a list of a plurality of instances of entities Which have been identified in the digital representation of a document, at least one of the listed instances of an entity having a user selectable user interface element associated therewith;

(iii) responsive to a user selecting the user selectable user interface element associated with an instance of an entity, adjusting the portion of the digital representation of a document which is displayed in the first region to include the location within the digital representation of a document where the instance of an entity associated with the selected user interface element is located:

(iv) highlighting instances of relations identified as being located within the portion of the digital representation of a document which is displayed in the first region at the identified location of the identified instances of relations;

(v) displaying in the second region of the display screen a list of a plurality of instances of relations which have been identified in the digital representation of a document, at least one of the listed instances of an relation having a user selectable user interface element associated therewith; and (vi) responsive to a user selecting the user selectable user interface element associated with an instance of a relation, adjusting the portion of the digital representation of a document which is displayed in the first region to include the location within the digital representation of a document where the instance of a relation associated with the selected user interface element is located.

14. A non-transitory computer-readable medium storing computer program code which, when executed by an computing apparatus, causes the computing apparatus to perform the method of claim 1.

* * * * *